US006225273B1

(12) United States Patent
Willey et al.

(10) Patent No.: US 6,225,273 B1
(45) Date of Patent: May 1, 2001

(54) PHOTOCHEMICAL SUPEROXIDE GENERATORS

(75) Inventors: Alan David Willey, Cincinnati, OH (US); Anthony Harriman, Bischheim (FR)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 09/355,156

(22) PCT Filed: Jan. 22, 1998

(86) PCT No.: PCT/US98/00224

§ 371 Date: Jul. 23, 1999

§ 102(e) Date: Jul. 23, 1999

(87) PCT Pub. No.: WO98/32829

PCT Pub. Date: Jul. 30, 1998

Related U.S. Application Data
(60) Provisional application No. 60/034,158, filed on Jan. 24, 1997.

(51) Int. Cl.[7] .............................. C11D 3/26; C11D 3/395; C09B 47/04
(52) U.S. Cl. ........................... 510/301; 540/128; 540/140
(58) Field of Search ........................... 510/301; 540/122, 540/128, 121, 140

(56) References Cited

U.S. PATENT DOCUMENTS

| | | | |
|---|---|---|---|
| 3,094,536 | 6/1963 | Kenney et al. | 260/314.5 |
| 3,927,967 | 12/1975 | Speakman | 8/103 |
| 4,033,718 | 7/1977 | Holcombe et al. | 8/103 |
| 4,166,718 | 9/1979 | Reinert et al. | 8/111 |
| 4,240,920 | 12/1980 | de Luque | 252/99 |
| 4,255,273 | 3/1981 | Sakkab | 252/102 |
| 4,256,597 | 3/1981 | Sakkab | 252/99 |
| 4,318,883 | 3/1982 | Polony et al. | 422/22 |
| 4,368,053 | 1/1983 | Eckhardt et al. | 8/102 |
| 4,497,741 | 2/1985 | Hölzle et al. | 260/245.77 |
| 4,648,992 | 3/1987 | Graf et al. | 540/124 |
| 5,679,661 | * 10/1997 | Willey | 514/63 |
| 5,916,481 | * 6/1999 | Willey | 252/186.21 |

FOREIGN PATENT DOCUMENTS

| | | | |
|---|---|---|---|
| 0 285965 | 10/1988 | (EP) | C09B/67/22 |
| 0 381211 | 8/1990 | (EP) | G11B/7/24 |
| 0 484027 | 5/1992 | (EP) | C09B/47/04 |
| 1372035 | 10/1974 | (GB) | D06L/3/04 |
| 1408144 | 1/1975 | (GB) | D06L/3/04 |
| 2159516 | 12/1985 | (GB) | C09B/47/04 |
| 6-73397 | 3/1994 | (JP) | C11D/3/395 |
| WO 91/18006 | 11/1991 | (WO) | C07J/43/00 |

OTHER PUBLICATIONS

Brasseur, N., et al., "Synthesis and Photodynamic Activities of Silicon 2,3–Naphthalocyanine Derivatives", J. Med. Chem., vol. 37, pp. 415–420 (1994).

Cook, M.J. et al., "Octa–alkoxy Phthalocyanine and Naphthalocyanine Derivatives: Dyes with Q–band Absorption in the Far Red or Near Infrared" J. Chem. Soc., Perkin Trans., vol. I., pp. 2453–2458 (1988).

Eberson, L., "Electron–Transfer Reactions in Organic Chemistry", Adv. Phys. Org. Chem., V. Gold/D. Bethell, Ed., vol. 18, pp. 79–185 (1982).

Esposito, J.N. et al., "The Synthesis and Physical Properties of Some Organo– and Organosiloxysilicon Phthalocyanines", Inorg. Chem., vol. 5, No. 11, pp. 1979–1984 (Nov. 1966).

Ford, W.E. et al., "Synthesis and Photochemical Properties of Aluminum, Gallium, Silicon, and Tin Naphthalocyanines", Inorg. Chem., vol. 31, pp. 3371–3377 (1992).

Hayashida, S., et al., "Effect of Axial Substituents on the Aggregate of Silicon Naphthalocyanine in the Vacuum Deposited Thin Films", Chem. Lett., pp. 2137–2140 (1990).

Joyner, R.D. et al, "Phthalocyaninosilicon Compounds", Inorg. Chem., vol. 1, No. 2, pp. 236–238 (May 1962).

Kavarnos, G. J., et a., "Photosensitization by Reversible Electron Transfer: Theories Experimental Evidence, and Examples", Chem. Rev., vol. 86, pp. 401–449 (1986).

Kroenke, W.E. et al., "The Infrared Spectra of Some Tin and Lead Phthalocyanines", Inorg. Chem. , vol. 3, No. 5, pp. 696–698 (May 1964).

Lopez, L., "Photoinduced Electron Transfer Oxygenations", Top. Current Chem., vol. 156, pp. 117–166 (1990).

Lowery, M.H. et al., "Dichloro(phthalocyanino)silicon", Inorg. Chem., vol. 4, p. 128 (1965).

Mariano, P.S., et al., "Synthetic Aspects of Photochemical Electron Transfer Reactions", Synthetic Organic Photochemistry, Wm. Horspool (Ed.) Plenum Press, NY, pp. 145–257 (1984).

Mattay, J., "Charge Transfer and Radical Ions in Photochemistry", Angew. Chem. Int. Ed. Engl, vol. 26, pp. 825–845 (1987).

Moyer, T. J., et al., "Iodine Doped $(SiNcO)_n$—A new Conducting Polymer", Polymer Preps, vol. 25, pp. 234–235 (1986).

Parker, V. D., "Reaction Pathways of the Cation Radicals of Aromatic Compounds Related to the Anthracenes", Acc. Chem. Res., vol. 17, pp. 243–250 (1984).

Rafaeloff, R., et al., "New Group IV Phthalocyanines", J. Inorg. Nucl. Chem., vol. 28, pp. 899–902 (1966).

Wen, T–C., et al., "Synthesis and Photoproperties of Silicon Phthalocyanines and Silicon Naphthalocyanines", J. Chin. Chem. Soc., vol. 40, pp. 141–147 (1993).

(List continued on next page.)

Primary Examiner—John Hardee
(74) Attorney, Agent, or Firm—Fay, Sharpe, Fagan, Minnich & McKee, LLP

(57) ABSTRACT

Disclosed are photochemical super oxide generators useful as photobleaches for laundry detergent compositions and as photobleaches or photodisinfectants for use in hard surface cleaning compositions. The compounds described herein comprise an amino-containing electron transfer moiety bonded to the photosensitizing unit wherein the amino-containing moiety is capable of transferring an electron to the photochemically excited π electron cloud of the photosensitizer unit thereby enabling superoxide formation.

18 Claims, No Drawings

OTHER PUBLICATIONS

Wheeler, B.L. et al., "A Silicon Phthalocyanine and a Silicon Naphthalocyanine; Synthesis, Electrochemistry, and Electrogenerated Chemiluminescence" J. Am. Chem. Soc., vol. 106, pp. 7404–7410 (1984).

Witkiewic, Z. et al., "Properties of Octamethoxyphthalocyanines I. On their syntheses, electrical conductivity, and catalytic activity", Material Science, vol. 11, No. 1–2, pp. 39–45 (1976).

* cited by examiner

PHOTOCHEMICAL SUPEROXIDE GENERATORS

This application claims the priority of U.S. Provisional Application 60/034,158, filed Jan. 24, 1997.

FIELD OF THE INVENTION

The present invention relates to photochemical superoxide generators and their use in laundry compositions and hard surface cleaning compositions comprising one or more of said photochemical superoxide generators, effective as a bleaching agent, stain remover, or bactericide. The present invention also relates to methods for cleaning fabric or hard surfaces, and for providing a means of sanitizing fabric or hard surfaces.

BACKGROUND OF THE INVENTION

It is known that certain water-soluble phthalocyanine, naphthalocyanine, mixed cyanine, and metallocyanine compounds can be used as photobleaching and antimicrobial agents. Phthalocyanines and naphthalocyanines or their metal complexes can form "singlet oxygen" an oxidative species capable of reacting with stains to bleach them to a colorless and usually water-soluble state.

It has now been surprisingly found that certain porphyrin, metalloporphyrin, phthalocyanine, naphthalocyanine, mixed cyanine, and metallocyanine compounds can photochemically produce superoxide. Superoxide is typically formed via non-photochemical means from the disproportionation of alkali and alkaline earth metal superoxides.

Superoxide is a reactive oxygen species formed by the one electron reduction of oxygen, has a longer lifetime than singlet oxygen and is capable of decolorizing (bleaching) stains and killing bacteria. Throughout this application superoxide is represented as $O_2^-$ based on common literature practice.

Surprisingly, it has been found that superoxide can be efficiently produced by photochemical means. Certain photosensitizing units which comprise a moiety capable of transfering an electron to the photochemically excited π electron cloud of the photosensitizer unit, are capable of producing superoxide. Preferably the photosensitizers, preferably porphyrins, metalloporphyrins, cyanines, and metallocyanines, and have the electron transfering moiety covalently attached.

It is therefore an aspect of the present invention to provide novel materials that photochemically produce superoxide. These materials are photosensitizing units which have covalently attached a moiety capable of transfering an electron to the excited state of the aforementioned photosensitizer. The superoxide produced by these compounds is useful in that the superoxide molecules are capable of acting as bleaching materials or as antimicrobials.

It is a further aspect of the present invention to provide laundry detergent and hard surface cleaning compositions comprising the aforementioned superoxide generators.

In accordance with still another aspect of the present invention, a method for removing stains from fabric and for killing bacteria as well as preventing the re-propagation of said bacteria is herein provided. The method comprises contacting the fabrics or surface contaminated with bacteria with an aqueous medium comprising at least 0.001 ppm of the photochemical superoxide generators described herein below. These, and other objects, features, and advantages will be clear from the following detailed description and the appended claims.

BACKGROUND ART

The following references relate to various aspects of superoxide and photochemical processes encompassed within the present invention: *Chem. Rev.*, Kavarnos G. J., Turro N. J., 86, pg. 401, (1986); *Angew. Chem. Int. Ed. Eng.*, Mattay J., 26, pg. 825, (1987); *Adv. Phys. Org. Chem.*, Eberson L., 18, pg. 79, (1987); *Top. Current Chem.*, Lopez, L., 156, pg. 117 (1990); *Adv. Photochem.*, Fox, M. S., 13, pg. 237, (1986); "Synthetic Organic Photochemistry", Horspool W. M. (ed); Mariano, P. S., pg. 145, (1984), Plenum Press, New York; "Organic Photochemistry", Padwa, A. (ed); Mattes, S. L. and Farid, S., 6, pg. 233, (1983); *Accounts of Chemical Research*, Parker, V. D., 17, pg. 243, (1984).

SUMMARY OF THE INVENTION

The present invention relates to photochemical superoxide generators having the formula:

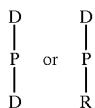

wherein P is a photosensitizing group; each D is independently a unit having the formula:

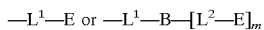

wherein B is a unit capable of providing a branch point; $L^1$ and $L^2$ are linking units; E units are electron transfer units having the formula:

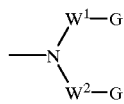

wherein each $W^1$ and $W^2$ is independently $C_1$–$C_4$ alkylene; G is hydrogen, an electron withdrawing group, and mixtures thereof; m is from 2 to 4; provided:
a) $L^1$, $L^2$, and B taken alone or in combination do not form a continuous series of conjugated bonds extending from the photosensitizing group P to the moiety E; and
b) the number of chemical bonds from photosensitizing group P to the E unit are no more than 20; and R is an axial moiety which mediates the solubility or substantivity of the superoxide generator.

It is also an object of the present invention to provide laundry detergent compositions comprising the photochemical superoxide generators described herein and methods for using said super oxide generators for bleaching fabric. The laundry detergent compositions comprise:
a) at least about 0.1% by weight, of a detersive surfactant;
b) at least about 0.001% of a source of superoxide; and
c) the balance carriers and adjunct ingredients.

It is a further object of the present invention to provide a hard surface cleaning compositions and a method for sanitizing a hard surface by contacting the superoxide generators described herein with a surface in need of cleaning or disinfecting.

It is yet a further object of the present invention to provide a method for bleaching fabric having stains or soils, or otherwise in need of bleaching, by contacting an aqueous solution of the photochemical superoxide generators of the present invention with said fabric.

All percentages, ratios and proportions herein are by weight, unless otherwise specified. All temperatures are in degrees Celsius (° C.) unless otherwise specified. All documents cited are in relevant part, incorporated herein by reference.

DETAILED DESCRIPTION OF THE INVENTION

The present invention relates to superoxide generators wherein the superoxide is induced by a photochemical means, that is superoxide is produced when the superoxide generator is exposed to a source of light. The resulting superoxide molecule which is generated therein has the capacity to act as an effective bleaching agent, disinfectant or bactericide.

The superoxide generators of the present invention have the formula:

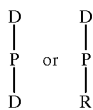

and comprise:
  a) a photosensitizing group;
  b) optionally a photoactive metal or non-metal;
  c) at least one moiety which is capable of transferring an electron to the excited state of the photosensitizing group; and
  d) optionally an axial moiety which mediates the solubility or substantivity of the superoxide generator molecule.

For the purposes of the present invention substituted aryl units are defined as moieties having the formula:

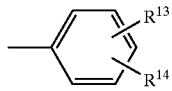

wherein $R^{13}$ and $R^{14}$ are independently selected from the group consisting of hydrogen, $C_1$–$C_6$ alkyl, $C_2$–$C_6$ alkenyl, $C_1$–$C_6$ alkoxy, $C_3$–$C_6$ branched alkoxy, halogen, morpholino, cyano, nitrilo, —$CO_2^-M^+$, —$SO_3^-M^+$, —$OSO_3^-M^+$, —$N(R^{15})_2$, and —$N^+(R^{15})_3X^-$ wherein each $R^{15}$ is independently hydrogen or $C_1$–$C_4$ alkyl; and mixtures thereof; wherein M is a water soluble cation and X is chlorine, bromine, iodine, or other water soluble anion. Examples of other water soluble anions include organic species such as fumarate, tartrate, oxalate and the like, inorganic species include sulfate, hydrogen sulfate, phosphate and the like.

For the purposes of the present invention substituted alkylenearyl units are defined as moieties having the formula:

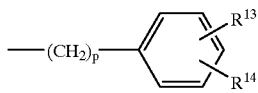

wherein $R^{13}$ and $R^{14}$ are the same as define above, p is from 1 to about 10.

For the purposes of the present invention substituted aryloxy units are defined as moieties having the formula:

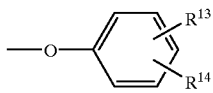

wherein $R^{13}$ and $R^{14}$ are the same as define above.

For the purposes of the present invention substituted alkyleneoxyaryl units are defined as moieties having the formula:

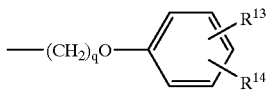

wherein $R^{13}$ and $R^{14}$ are the same as define above, q is from 0 to about 10.

For the purposes of the present invention substituted oxyalkylenearyl units are defined as moieties having the formula:

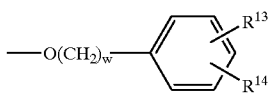

wherein $R^{13}$ and $R^{14}$ are the same as define above, w is from 1 to about 10.

For the purposes of the present invention both substituted and un-substituted aryl, alkylenearyl, aryloxy, and oxyalkylenearyl have the indices p, q, and w as defined herein above.

For the purposes of the present invention substituted alkyl units are defined as moieties having the formula

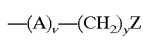

wherein A is the heteroatom nitrogen or oxygen, preferably A is oxygen, the index v is 0 when the heteroatom is absent, v is equal to 1 when the heteroatom is present, Z is hydroxy, nitrilo, cyano, $C_1$–$C_6$ alkoxy, aryl; substituted aryl, aryloxy, and substituted aryloxy as defined above; alkyleneamino as further defined herein below; hydroxyl, —$SO_3^-M^+$, —$OSO_3^-M^+$, —$CO_2H$, —$N(R^{15})_2$, and mixtures thereof; each $R^{15}$ is independently hydrogen or $C_1$–$C_4$ alkyl, M is a water soluble cation; y is from 0 to 22.

For the purposes of the present invention alkylethyleneoxy units are defined as moieties having the formula:

wherein A is the heteroatom nitrogen or oxygen, preferably A is oxygen, the index v is 0 when the heteroatom is absent, v is equal to 1 when the heteroatom is present, Z is hydrogen, $C_1$–$C_6$ alkoxy, aryl, substituted aryl, aryloxy, substituted aryloxy, alkyleneamino, —$SO_3^-M^+$, —$OSO_3^-M^+$, —$CO_2H$, and mixtures thereof; x is from 1 to 100 and y is from 1 to 12.

For the purposes of the present invention alkyleneamino units are defined as moieties having the formula:

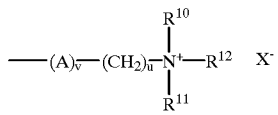

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof, A is the heteroatom nitrogen or oxygen, preferably A is oxygen, the index v is 0 when the heteroatom is absent, v is equal to 1 when the heteroatom is present, X is chloride, bromide, iodide, or other water soluble anion, u is from 0 to 22. Examples of other water soluble anions include organic species such as fumarate, tatrate, oxalate and the like, inorganic species include sulfate, hydrogen sulfate, phosphate and the like.

For the purposes of the present invention amino units are defined as moieties having the formula:

wherein $R^{17}$ and $R^{18}$ are $C_1$–$C_{22}$ alkyl, $C_3$–$C_{22}$ branched alkyl $C_2$–$C_{22}$ alkenyl, $C_3$–$C_{22}$ branched alkenyl, or mixtures thereof.

For the purposes of the present invention $C_1$–$C_{18}$ linear or branched alkylene moieties are defined as units having the formula:

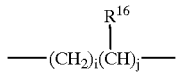

wherein $R^{16}$ is $C_1$–$C_4$ alkyl; the index i has the value from 1 to 18, the index j has the value from 1 to 18, and the value of i+j can not exceed 18.

For the purposes of the present invention $C_1$–$C_{18}$ linear or branched alkenylene moieties are defined as moieties comprising one or more units, or combinations of units having the formula:

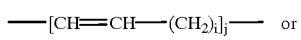
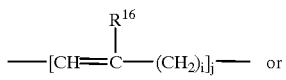
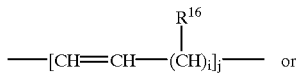
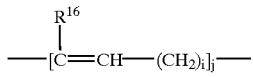

wherein $R^{16}$ is $C_1$–$C_4$ alkyl; the index i has the value from 1 to 14, the index j has the value from 1 to 6, provided the number of covalent bonds in the backbone, excluding the bonds which comprise $R^{16}$ does not exceed 18.

For the purposes of the present invention $C_1$–$C_{18}$ linear or branched alkyleneoxy moieties which comprise the $L^1$ or $L^2$ units described herein below, are defined as units or a combination of units having the formula:

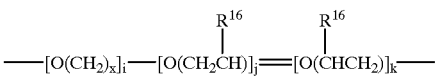

wherein $R^{16}$ is $C_1$–$C_4$ alkyl; the index x has the value from 2 to 4; i has the value from 1 to 6, the index j has the value from 1 to 6, the index k has the value from 1 to 6, and the value of i+j+k can not exceed 6 if x is equal to 2; if x is greater than 2 the number of bonds which comprise the alkyleneoxy moiety cannot exceed 18.

For the purposes of the present invention $C_1$–$C_{18}$ substituted or unsubstituted arylene moieties are defined as 1,2-phenylene, 1,3-phenylene, and 1,4-phenylene units having the formula:

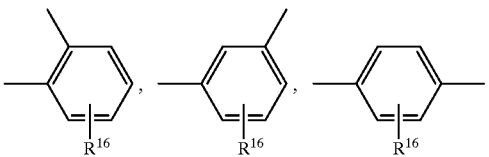

wherein $R^{16}$ is hydrogen, $C_1$–$C_4$ alkyl, and mixtures thereof.

For the purposes of the present invention $C_1$–$C_{18}$ substituted or unsubstituted alkylenearylene moieties are defined as 1,2-phenylene, 1,3-phenylene, and 1,4-phenylene units having the formula:

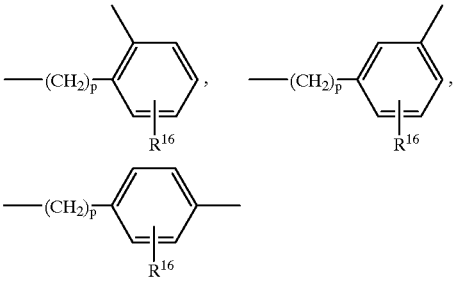

wherein $R^{16}$ is hydrogen, $C_1$–$C_4$ alkyl, and mixtures thereof, the index p has the value from 1 to 12.

For the purposes of the present invention $C_1$–$C_{18}$ substituted and unsubstituted aryleneoxy moieties are defined as 1,2-phenyleneoxy, 1,3-phenyleneoxy, and 1,4-phenyleneoxy units having the formula:

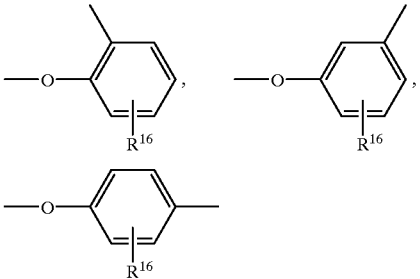

wherein $R^{16}$ is hydrogen, $C_1$–$C_4$ alkyl, and mixtures thereof.

For the purposes of the present invention $C_1$–$C_{18}$ substituted and unsubstituted oxyalkylenearylene moieties are defined as 1,2-oxyalkylenephenylene, 1,3- oxyalkylenephenylene, and 1,4-oxyalkylenephenylene units having the formula:

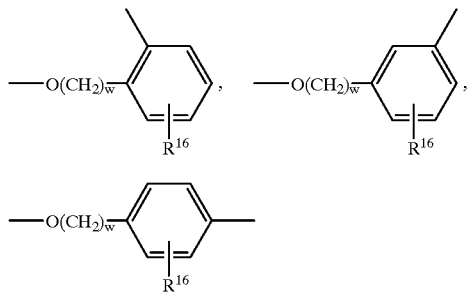

wherein $R^{16}$ is hydrogen, $C_1$–$C_4$ alkyl, and mixtures thereof, the index w has the value from 1 to 11.

For the purposes of the present invention $C_1$–$C_{18}$ substituted and unsubstituted alkyleneoxyarylene moieties are defined as 1,2-alkyleneoxyphenylene, 1,3-alkyleneoxyphenylene, and 1,4-alkyleneoxyphenylene units having the formula:

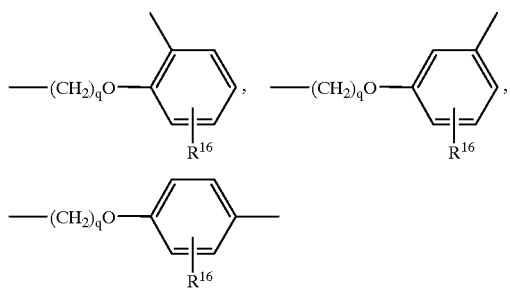

wherein $R^{16}$ is hydrogen, $C_1$–$C_4$ alkyl, and mixtures thereof, the index q has the value from 1 to 11.

Photosensitizing Groups

The superoxide generators of the present invention comprise a photosensitizer group. Preferred photosensiting groups P are the cyanines and metallocyanines. The cyanine photosensitizing groups include phthalocyanines, naphthalocyanines, mixed cyanines as well as other aromatic photosensitizing units described herein below. Preferably the photosensitizing groups are combined with a photoactive metal or non-metal to produce a metallocyanine photosensitizer. However, the photosensitizing groups of the present invention must be capable of being electrochemically reduced, that is they must be capable of receiving an electron from the "electron transferred unit" E described further herein below.

When the photosensitizing group P is a cyanine ring said ring has the formula:

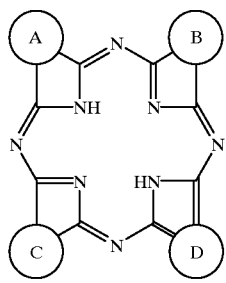

wherein rings A, B, C, and D are aromatic rings independently selected from the group consisting of substituted and unsubstituted benzene, substituted and unsubstituted naphthalene, substituted and unsubstituted anthracene, substituted and unsubstituted phenanthrene, and mixtures thereof.

For the purposes of the present invention cyanine ring components derived from substituted and unsubstituted benzene can be written in either of two equivalent resonance formulas:

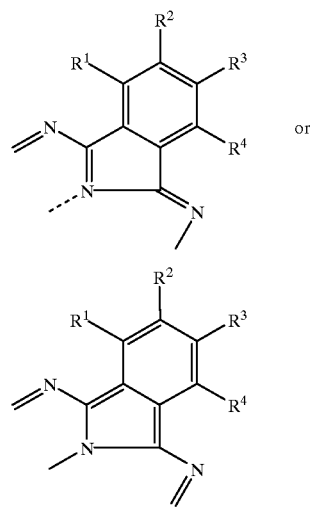

wherein $R^1$, $R^2$, $R^3$ and $R^4$ are each independently selected from the substituents described herein below.

For the purposes of the present invention cyanine ring components derived from substituted and unsubstituted 2,3-naphthylene can be written in either of two equivalent resonance formulas:

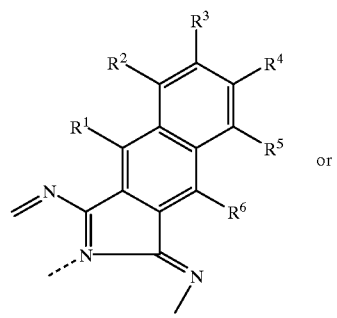

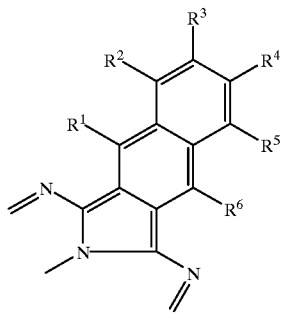

wherein $R^1$, $R^2$, $R^3$, $R^4$, $R^5$, and $R^6$ are independently selected from the substituents described herein below.

For the purposes of the present invention cyanine ring components derived from substituted and unsubstituted 1,2-naphthylene can be written in either of two equivalent resonance formulas:

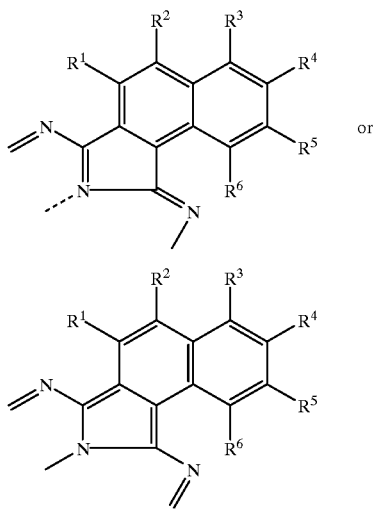

wherein $R^1$, $R^2$, $R^3$, $R^4$, $R^5$, and $R^6$ units arm independently selected from the substituents listed herein below.

For the purposes of the present invention cyanine ring components derived from substituted and unsubstituted anthracene can be written in either of two equivalent resonance formulas:

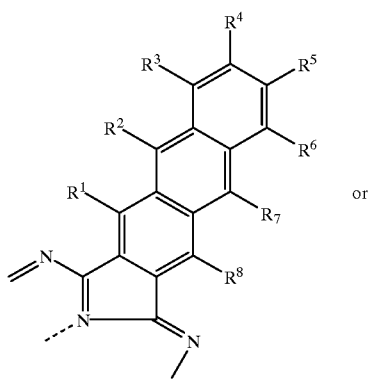

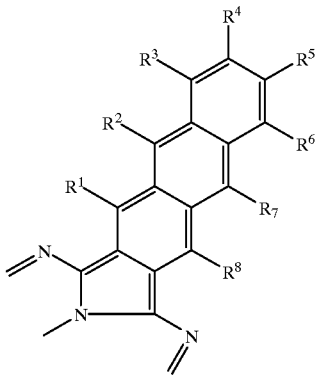

wherein $R^1$, $R^2$, $R^3$, $R^4$, $R^5$, $R^6$, $R^7$, and $R^8$ units are independently selected from the substituents described herein below.

For the purposes of the present invention cyanine ring components derived from substituted and unsubstituted phenanthrene can be written in either of two equivalent resonance formulas:

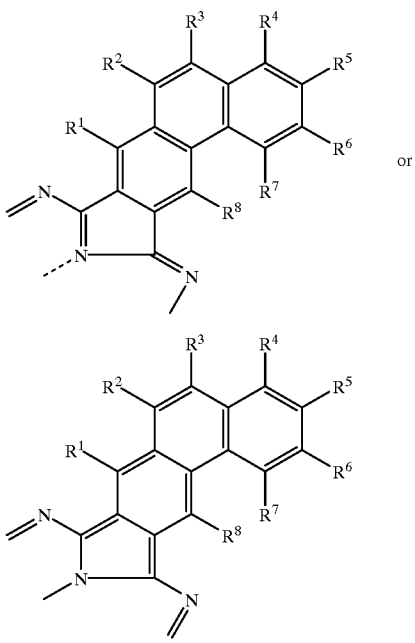

wherein $R^1$, $R^2$, $R^3$, $R^4$, $R^5$, $R^6$, $R^7$, and $R^8$ units are independently selected from the substituents described herein below.

For the purposes of the present invention each $R^1$, $R^2$, $R^3$, $R^4$, $R^5$, $R^6$, $R^7$, and $R^8$ unit is independently selected from the group consisting of:

a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;

g) $C_1$–$C_{22}$ alkoxy;
h) branched alkoxy having the formula:

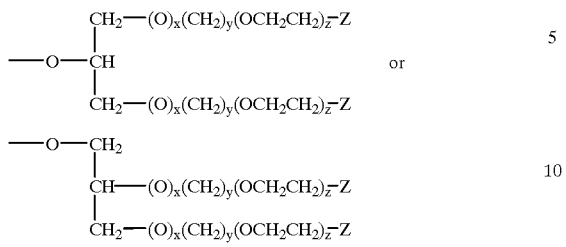

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  iii) polyhydroxyl substituted $C_3$–$C_{22}$ alkyl;
  iv) $C_3$–$C_{22}$ glycol;
  v) $C_1$–$C_{22}$ alkoxy;
  vi) $C_3$–$C_{22}$ branched alkoxy;
  vii) substituted aryl, unsubstituted aryl, or mixtures thereof;
  viii) substituted alkylenearyl, unsubstituted alkylenearyl, or mixtures thereof;
  ix) substituted aryloxy, unsubstituted aryloxy, or mixtures thereof;
  x) substituted oxyalkylenearyl, unsubstituted oxyalkylenearyl, or mixtures thereof;
  xi) substituted alkyleneoxyaryl, unsubstituted alkyleneoxyaryl, or mixtures thereof;
p) an alkyleneamino unit of the formula:

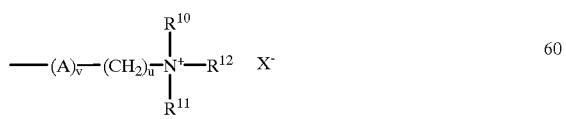

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof; $R^{12}$ is:
  i) hydrogen;
  ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  A is nitrogen or oxygen; X is chlorine, bromine, iodine, or other water soluble anion, v is 0 or 1, u is from 0 to 22;
q) an amino unit of the formula:

—$NR^{17}R^{18}$ wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
r) an alkylethyleneoxy unit of the formula:

—$(A)_v$—$(CH_2)_y(OCH_2CH_2)_xZ$ wherein Z is:
  i) hydrogen;
  ii) hydroxyl;
  iii) —$CO_2H$;
  iv) —$SO_3^-M^+$;
  v) —$OSO_3^-M^+$;
  vi) $C_1$–$C_6$ alkoxy;
  vii) substituted aryl, unsubstituted aryl, or mixtures thereof;
  viii) substituted aryloxy, unsubstituted aryloxy, or mixtures thereof;
  ix) alkyleneamino; or mixtures thereof;
  A is nitrogen or oxygen, M is a water soluble cation, v is 0 or 1, x is from 0 to 100, y is from 0 to 12;
s) substituted siloxy of the formula:

—$OSiR^{19}R^{20}R^{21}$ wherein each $R^{19}$, $R^{20}$, and $R^{21}$ is independently
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) substituted aryl, unsubstituted aryl, or mixtures thereof;
  iii) substituted aryloxy, unsubstituted aryloxy, or mixtures thereof;
  iv) an alkylethyleneoxy unit of the formula:

—$(A)_v$—$(CH_2)_y(OCH_2CH_2)_xZ$ wherein Z is:
  a) hydrogen;
  b) hydroxyl;
  c) —$CO_2H$;
  d) —$SO_3^-M^+$;
  e) —$OSO_3^-M^+$;
  f) $C_1$–$C_6$ alkoxy;
  g) substituted aryl, unsubstituted aryl, or mixtures thereof;- h) substituted aryloxy, unsubstituted aryloxy, or mixtures thereof;

i) alkyleneamino; or mixtures thereof;

A is nitrogen or oxygen, M is a water soluble cation, v is 0 or 1, x is from 0 to 100, y is from 0 to 12; or mixtures thereof; and mixtures thereof;

A non-limiting example of the photosensitizing ring P is the unsubstituted phthalocyanine moiety having the formula:

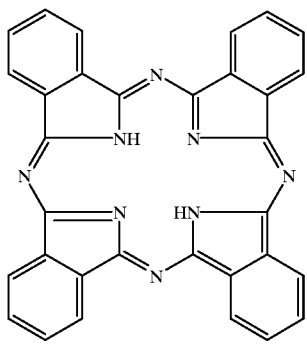

wherein the $R^1$, $R^2$, $R^3$, and $R^4$ units of each benzene ring is a hydrogen atom.

A further example of the photosensitizing ring P is the unsubstituted 2,3-naphthalocyanine moiety having the formula:

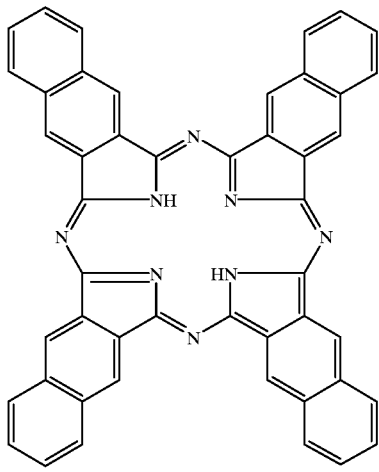

wherein the $R^1$, $R^2$, $R^3$, $R^4$, $R^5$, and $R^6$ units of each naphthylene ring is a hydrogen atom.

However, the photosensitizing ring can be comprised of more than one type of substituted or unsubstituted unit. This mixture of units results in the formation of a hybrid cyanine photosensitizing group. A non-limiting example of a "hybrid cyanine" or "mixed cyanine" ring system is the unsubstituted (3)-benzene-(1)-naphthalene ring having the formula:

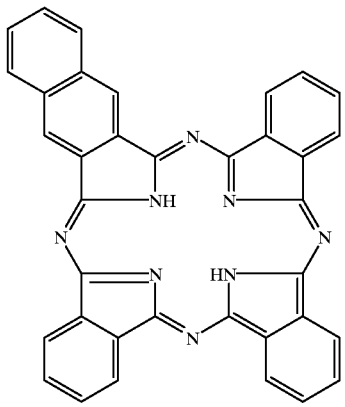

wherein the $R^1$, $R^2$, $R^3$, and $R^4$ units of each of the benzene rings is a hydrogen atom, and the $R^1$, $R^2$, $R^3$, $R^4$, $R^5$, and $R^6$ units of the naphthalene ring is a hydrogen atom.

The term "hybrid cyanine" is taken to encompass all the reaction products formed when two or more monomers are reacted together. Those skilled in the art will recognize that the resulting mixture contains non-hybrid structures as well, however, these non-hybrid structures fall within the definition of "hybrid cyanines" for the purposes of the present invention. It will also be recognized that as the number of different monomers increases, the number of possible hybrid rings formed also increases.

As indicated above, the "hybrid cyanines" can be formed by reacting together different monomers. In addition, the stoichiometric ratio of those monomers can be varied. The following provides non-limiting examples of reactions to form mixed cyanines.

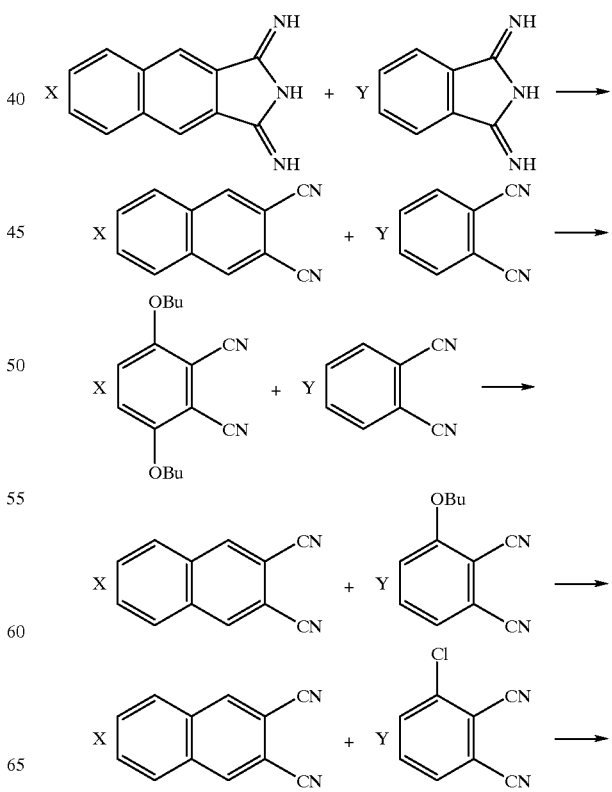

-continued

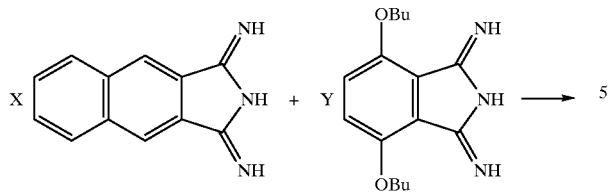

wherein the ratio of the indices x and y indicate the stoichiometric amounts of each reactant said reactant ratios can range from 0.01 to 100, that is the value of x can be 1 when the value of y is 100 and the value of x can be 100 when the value of y is 1. The following formula

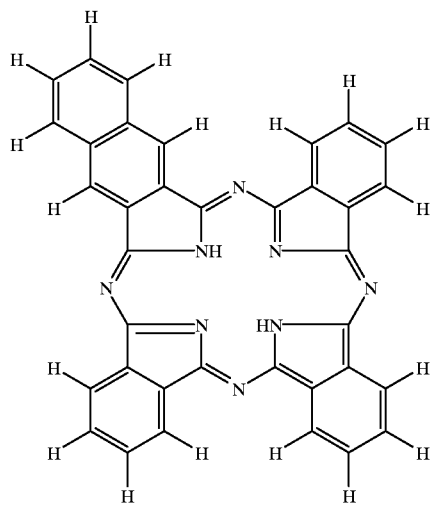

is a major product from the following reaction stoichiometry

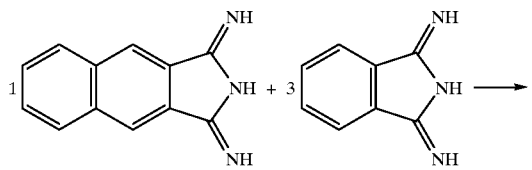

Preferably the cyanine and hybrid cyanines are combined with a photoactive metal or non-metal. What is meant by a "photoactive" metal or non-metal is any atom which when combined with a photosensitizing unit according to the present invention further enhances the photophysics of the photosensitizer unit. Preferred photoactive metals and non-metals include, but are not limited to, silicon, aluminum, phosphorous, tin, germanium, platinum, palladium, lead, cadmium, zinc, and mixtures thereof. However, any photoactive metal or non-metal is suitable for use in combination with the photosensitizer groups of the present invention provided said photoactive metal or non-metal has a valence of at least greater than 3. Metals or non-metals which are not suitable for use in the present invention are the paramagnetic atoms inter alia iron, copper, chromium, and cobalt.

Further suitable photosensitizing group are the porphyrins and metalloporphyrins having the formula:

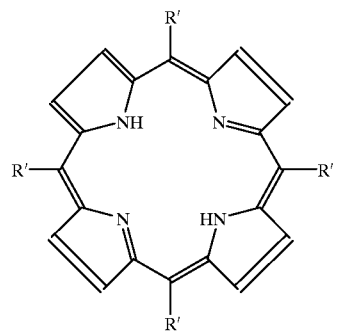

wherein R' is aryl, substituted aryl, and mixtures thereof, as defined herein above.

Electron Transfer Moiety

The photochemical superoxide generators of the present invention must comprise an Electron Transfer Moiety. For the purposes of the present invention the term "electron transfer moiety" is defined as "a moiety which is capable of transferring an electron to the photosensitizer group P when the photosensitizer is in an excited state". Put in other terms, the transfer of an electron from the transferring moiety to the photochemically excited state of the photosensitizer group is a process that is key to the production of superoxide.

This electron transfer process in normally a very rapid and reversible process. However, for the E units of the present invention this transfer is not reversible. Not wishing to be limited by theory, when an electron is transferred by an "electron transfer unit" as described herein, the E unit is modified in such a way (typically by chemical fragmentation) that the E unit can no longer re-accept the transferred electron and therefore the process is a one way transfer. The donor moiety decomposes prior to re-transfer of the electron. Once the transfer is complete the formation of superoxide ensues. When all the "electron transfer units" are exhausted, the remaining photoactive material is still capable of producing "singlet oxygen" another type of photochemical bleaching or disinfecting agent.

According to the present invention electron transfer moieties are comprised of an electron transfer unit E and a suitable unit for linking the E unit to the photosensitizer unit P. Electron transfer moieties have the formula:

$$-L^1-E \text{ or } -L^1-B-[L^2-E]_m$$

wherein $L^1$ and $L^2$ are linking units and B is an atom capable of providing from 2 to 4 branch points. The index m has the value from 2 to 4. B units have the following formulae:

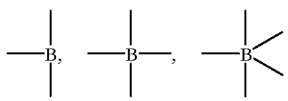

wherein preferably B is selected from the group consisting of boron, aluminum, nitrogen, phosphorous, carbon, silicon, tin, germanium, and mixtures thereof, more preferably carbon, silicon, and nitrogen.

$L^1$ and $L^2$ are linking units wherein $L^1$ and each $L^2$ are independently selected from the group consisting of oxygen, $C_1$–$C_{18}$ linear or branched alkylene, $C_1$–$C_{18}$ linear or branched alkenylene; $C_1$–$C_{18}$ linear or branched alkyleneoxy, $C_1$–$C_{18}$ substituted or unsubstituted arylene, $C_1$–$C_{18}$ substituted or unsubstituted alkylenearylene, $C_1-C_{18}$ substituted or unsubstituted aryleneoxy, $C_1-C_{18}$ substituted or unsubstituted oxyalkylenearylene, $C_1-C_{18}$ substituted or unsubstituted alkyleneoxyarylene, and mixturs thereof, said units defined herein above.

For the purposes of the present invention an oxygen molecule may serve as a suitable $L^1$ unit, preferably when directly bonded to a branching unit to form a moiety having the general formula:

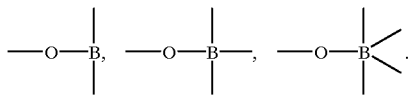

E units are electron transfer units having the formula:

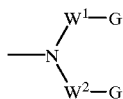

wherein each $W^1$ and $W^2$ is independently $C_1-C_4$ alkylene.

G is hydrogen, an electron withdrawing group, and mixtures thereof; preferably G is selected from the group consisting of halogen, nitro, cyano, substituted or unsubstituted phenyl, hydroxyl, alkoxy, $-CO_2R^{29}$, $-CO_2M$, $-SO_3M$, $-OSO_3M$, $-PO_3M$, $-OPO_3M$, $-CON(R^{29})_2$ wherein $R^{29}$ is hydrogen, $C_1-C_{12}$ alkyl; alkyleneoxy units having the formula:

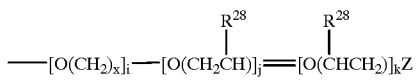

wherein $R^{28}$ is $C_1-C_4$ alkyl; Z is hydrogen, $C_1-C_{22}$ alkoxy, aryl, substituted aryl, aryloxy, substituted aryloxy, alkyleneamino, $-SO_3^-M^+$, $-OSO_3^-M^+$, $-CO_2H$, and mixtures thereof; the index x has the value from 1 to 4; i has the value from 0 to 20, the index j has the value from 0 to 20, the index k has the value from 0 to 20; alkyleneamino units having formula:

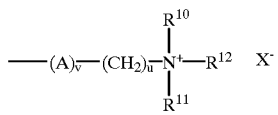

wherein $R^{10}$, and $R^{11}$ are each a $C_1-C_{22}$ alkyl, $C_3-C_{22}$ branched alkyl, $C_2-C_{22}$ alkenyl, $C_3-C_{22}$ branched alkenyl, $R^{12}$ is hydrogen, $C_1-C_{22}$ alkyl, $C_3-C_{22}$ branched alkyl, $C_2-C_{22}$ alkenyl, $C_3-C_{22}$ branched alkenyl and mixturts thereof, A is the heteroatom nitrogen or oxygen, preferably A is oxygen, the index v is 0 when the heteroatom is absent, v is equal to 1 when the heteroatom is present, X is chloride, bromide, iodide, or other water soluble anion, u is from 0 to 22; more preferably G is:

a) $C_1-C_{16}$ alkoxy;
b) hydroxy;
c) $-CO_2R^{29}$;
d) $-CO_2M$;
e) $-SO_3M$;
f) ethyleneoxy of the formula:

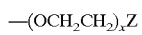

wherein Z is:
i) hydrogen;
ii) hydroxyl;
iii) $C_1-C_{22}$ alkoxy
iv) $-CO_2M$;
v) $-CH_2CO_2M$;
vi) $-SO_3M$;
vii) $-OSO_3M$; or
viii) alkyleneamino;

M is hydrogen, a water soluble cation or mixtures thereof; x is from 1 to 20.

The value of the index m depends on the nature of the branching unit B and can have the value from 2 to 4, preferably 3.

The electron transfer moieties of the present invention must not comprise more than twenty bonds between the point of attachment to the photosensitizer unit and the point of attachment to the E electron transfer unit, and the bonds comprising the link between the amino moiety and the photosensitizer group P must not comprise a series of conjugated bonds. Stated in other terms; "$L^1$, $L^2$, and B taken alone or in combination do not form a continuous series of conjugated bonds extending from the photosensitizing group P to the moiety E and the number of chemical bonds from photosensitizing group P to the nitrogen moiety are no more than 20 in number".

The following are non-iimiting examples of electron transfer moieties suitable for use in the present invention.

The following is an example wherein $L^1$ is a linear alkylene unit and comprises six non-onjugated bonds between the photosensitizer group P and the E unit; E is a dihydroxyallylamine wherein $W^1$ and $W^2$ are each hydroxyethyl, having the formula:

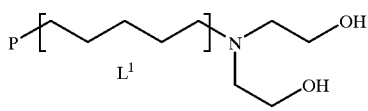

The following is an example wherein $L^1$ is an alkyleneoxy unit comprising 3 ethyleneoxy units, B is a methine carbon branch point, each $L^2$ is ethylene, the $L^1$, $L^2$, and B units taken together comprises thirteen non-conjugated bonds between the photosensitizer group P and the E unit; E is a dihydroxyalkylamine wherein $W^1$ and $W^2$ are each hydroxyethyl, having the formula:

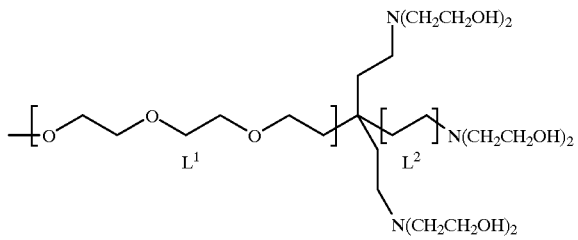

Axial R Units

The photochemical superoxide generators of the present invention optionally comprise axial R units covalently bonded to the central metal atom, wherein each R is independently selected from the group consisting of:

a) hydrogen;
b) halogen;
c) hydroxyl;

d) cyano;
e) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
g) polyhydroxyl substituted $C_3$–$C_{22}$ alkyl;
h) $C_1$–$C_{22}$ alkoxy;
i) branched alkoxy having the formula

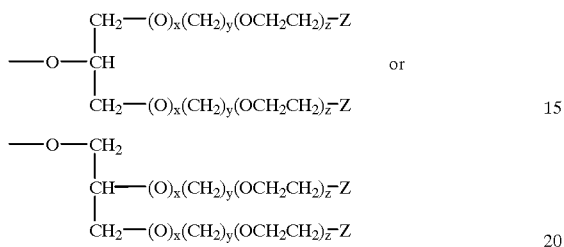

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, preferably from 0 to 3; each z independently has the value from 0 to 100, preferably from 0 to about 10, more preferably from 0 to about 7;
j) substituted aryl, unsubstituted aryl, or mixtures thereof;
k) substituted alkylenearyl, unsubstituted alkylenearyl or mixtures thereof;
l) substituted aryloxy, unsubstituted aryloxy, of mixtures thereof;
m) substituted oxyalkylenearyl, unsubstituted oxyalkylenearyl, or mixtures thereof;
n) substituted alkyleneoxyaryl, unsubstituted alkyleneoxyaryl, or mixtures thereof;
o) $C_1$–$C_{22}$ thioalkyl, $C_3$–$C_{22}$ substituted thioalkyl, and mixtures thereof;
p) alkyleneamino units;
q) an amino unit of the formula

—$NR^{17}R^{18}$ wherein $R^{17}$ and $R^{18}$ comprises $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;
r) alkylethyleneoxy units having the formula:

—(A)$_k$—(CH$_2$)$_m$(OCH$_2$CH$_2$)$_n$Z wherein A is the heteroatom nitrogen or oxygen, preferably A is oxygen, the index k is 0 when the heteroatom is absent, k is equal to 1 when the heteroatom is present, Z is:
i) hydrogen;
ii) hydroxyl;
iii) —$CO_2H$;
iv) —$CH_2CO_2M$;
v) —$SO_3^-M^+$;
vi) —$OSO_3^-M^+$;
vii) $C_1$–$C_{30}$ alkoxy;
viii) substituted aryl, unsubstituted aryl, or mixtures thereof;
ix) substituted aryloxy, unsubstituted aryloxy, or mixtures thereof;
x) alkyleneamino; and mixtures thereof;
A comprises nitrogen or oxygen, M is a water soluble cation, v is 0 or 1, x is from 0 to 100, y is from 0 to 12; preferably Z is hydrogen or $C_1$–$C_{30}$ alkoxy; n is from 1 to 100, preferably from 0 to about 20, more preferably from 2 to about 10; and m is from 1 to 12, preferably from about 1 to about 5;
s) carboxylate of the formula

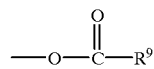

wherein $R^9$ comprises:
i) $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;
iii) poly-hydroxyl substituted $C_3$–$C_{22}$ alkyl;
iv) $C_3$–$C_{22}$ glycol;
v) $C_1$–$C_{22}$ alkoxy;
vi) $C_3$–$C_{22}$ branched alkoxy;
vii) substituted aryl, unsubstituted aryl, or mixtures thereof;
viii) substituted alkylaryl, unsubstituted alkylaryl, or mixtures thereof;
ix) substituted aryloxy, unsubstituted aryloxy, or mixtures thereof;
x) substituted alkoxy, unsubstituted alkoxyaryl, or mixtures thereof,
xi) substituted alkyleneoxyaryl, unsubstituted alkyleneoxyayl, of mixtures thereof;
t) siloxy and substituted siloxy of the formula —$OSiR^{19}R^{20}R^{21}$ wherein each $R^{19}$, $R^{20}$, and $R^{21}$ is independently selected from the group consisting of:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

—(A)$_v$—(CH$_2$)$_y$(OCH$_2$CH$_2$)$_x$Z;

wherein Z comprises:
a) hydrogen;
b) $C_1$–$C_{30}$ alkyl,
c) hydroxyl;
d) —$CO_2M$;
e) —$CH_2CO_2M$;
f) —$SO_3^-M^+$;
g) —$OSO_3^-M^+$;
h) $C_1$–$C_6$ alkoxy;
i) substituted aryl, unsubstituted aryl, or mixtures thereof;
j) substituted aryloxy, unsubstituted aryloxy, or mixtures thereof;
k) alkyleneamino; or mixtures thereof;

A units comprise nitrogen or oxygen, M is a water soluble cation, v is 0 or 1, x is from 0 to 100, y is from 0 to 12;

and mixtures thereof.

According to the present invention the preferred axial R units comprise moieties having the formula

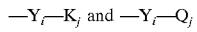

wherein Y is a linking moiety selected from the group consisting of O, $CR^{25}R^{26}$, $OSiR^{25}R^{26}$, $OSnR^{25}R^{26}$, and mixtures thereof; wherein $R^{25}$ and $R^{26}$ are hydrogen, $C_1$–$C_4$ alkyl, halogen, and mixtures thereof; i is 0 or 1, j is from 1 to 3;

K is a ligand selected from the group consisting of:
a) $C_1$–$C_{30}$ linear alkyl, $C_3$–$C_{30}$ branched alkyl, $C_2$–$C_{30}$ linear alkenyl, $C_3$–$C_{30}$ branched alkenyl, $C_6$–$C_{20}$ aryl, $C_7$–$C_{20}$ arylalkyl, $C_7$–$C_{20}$ alkylaryl, and mixtures thereof;
b) an alkylethyleneoxy unit of the formula

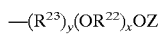

wherein Z is selected from the group consisting of hydrogen, $C_1$–$C_{20}$ alkyl, $C_3$–$C_{20}$ branched alkyl, $C_2$–$C_{20}$ linear alkenyl, $C_3$–$C_{20}$ branched alkenyl, $C_6$–$C_{20}$ aryl, $C_7$–$C_{30}$ arylalkyl, $C_6$–$C_{20}$ alkylaryl, and mixtures thereof; $R^{22}$ is selected from the group consisting of $C_1$–$C_4$ linear alkylene, $C_3$–$C_4$ branched alkylene, $C_3$–$C_6$ hydroxyalkylene, and mixtures thereof; $R^{23}$ is selected from the group consisting of $C_2$–$C_{20}$ alkylene, $C_3C_{20}$ branched alkylene, $C_6$–$C_{20}$ arylene, $C_7$–$C_{30}$ arylalkylene, $C_7$–$C_{30}$ alkylarylene, and mixtures thereof; x is from 1 to 100; y is 0 or 1; and Q is an ionic moiety having the formula:

wherein $R^{24}$ is selected from the group consisting of $C_3$–$C_{30}$ linear alkylene, $C_3$–$C_{30}$ branched alkylene, $C_2$–$C_{30}$ linear alkenylene, $C_3$–$C_{30}$ branched alkenylene, $C_6$–$C_{16}$ arylene, and mixtures thereof; W is selected from the group consisting of $-CO_2^-M^+$, $-SO_3^-M^+$, $-OSO_3^-M^+$; $PO_3^{2-}M^+$, $-OPO_3^-M^+$, alkyleneamino; M is a water soluble cation of sufficient charge to provide electronic neutrality and X is a water soluble anion as defined herein above.

Preferred axial R units are alkyl alkyleneoxy units of the formula

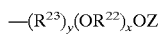

wherein Z is selected from the group consisting of hydrogen, $C_7$–$C_{20}$ linear alkyl, $C_3$–$C_{20}$ branched alkyl, $C_2$–$C_{20}$ linear alkenyl, $C_3$–$C_{20}$ branched alkenyl, $C_6$–$C_{10}$ aryl, $C_7$–$C_{20}$ arylalkyl, $C_7$–$C_{20}$ alkylaryl, and mixtures thereof; $R^{22}$ is selected from the group consisting of $C_1$–$C_4$ linear alkylene, $C_3$–$C_4$ branched alkylene, and mixtures thereof; $R^{23}$ is selected from the group consisting of $C_2$–$C_6$ alkylene, $C_3$–$C_6$ branched alkylene, $C_6$–$C_{10}$ arylene, and mixtures thereof; x is from 1 to 50; y is 0 or 1.

More preferred axial R units comprise y equal to 0, Z is hydrogen, $C_1$–$C_{20}$ alkyl, $C_3$–$C_{20}$ branched alkyl, $C_6$–$C_{10}$ aryl, and mixtures thereof, most preferred Z is hydrogen or $C_6$–$C_{20}$ linear alkyl, $C_{10}$–$C_{20}$ branched alkyl; $R^{22}$ is $C_1$–$C_4$ linear or $C_3$–$C_4$ branched alkylene.

Also preferred R units having the formula:

wherein Y is a linking moiety selected from the group consisting of O, $CR^{25}R^{26}$ $OSiR^{25}R^{26}$, $OSnR^{25}R^{26}$, and mixtures thereof; i is 0 or 1, j is from 1 to 3; Q is an ionic moiety having the formula:

wherein $R^{24}$ is selected from the group consisting of $C_2$–$C_{20}$ linear alkylene, $C_3$–$C_{20}$ branched alkylene, $C_2$–$C_{20}$ linear alkenylene, $C_3$–$C_{20}$ branched alkenylene, $C_6$–$C_{10}$ arylene, and mixtures thereof; W is selected from the group consisting of $-CO_2^-M^+$, $-SO_3^-M^+$, $-OSO_3^-M^+$; $PO_3^{2-}M^+$, $-OPO_3^-M^+$, alkyleneamino; M is a water soluble cation of sufficient charge to provide electronic neutrality and X is a water soluble anion as defined herein above.

A preferred hydrophilic R has the index i equal to 1; $R^{24}$ is $C_3$–$C_{20}$ linear alkylene, $C_3$–$C_{20}$ branched alkylene; P is $-CO_2^-M^+$, $-SO_3^-M^+$, $-OSO_3^-M^+$; M is a water soluble cation of sufficient charge to provide electronic neutrality.

Examples of Y units suitable for use in R units having the formula:

have the formula

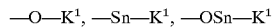

wherein i is equal to 1 and j is equal to 1. Further examples have the formula

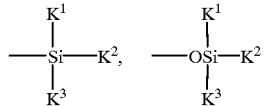

wherein i is equal to 1 and j is equal to 3. The above examples also apply to Y units when used with Q ionic moieties.

The present invention also relates to laundry detergent compositions comprising:
a) at least about 0.1%, preferably from about 0.1% to about 30%, more preferably from about 1% to about 30%, most preferably from about 5% to about 20% by weight, of a detersive surfactant, said detersive surfactant is selected from the group consisting of anionic, cationic, nonionic, zwitterionic, ampholytic surfactants, and mixtures thereof;
b) at least about 0.001 ppm, preferably from about 0.01 to about 10000 ppm, more preferably from about 0.1 to about 5000 ppm, most preferably form about 10 to about 1000 ppm, of a source of superoxide, preferably a super oxide generator having the formula

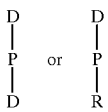

wherein P is a photosensitizing group; each D is independently a moiety which is capable of enhancing the production of singlet oxygen, as described herein above; and R is an axial moiety which mediates the solubility or substantivity of the super oxide generator as described herein above; and c) the balance carriers and adjunct ingredients.

It is also an object of the present invention to provide hard surface cleaning compositions which can be used to clean or disinfect hard surfaces, said compositions comprising:

a) at least about 0.1%, preferably from about 0.1% to about 30%, more preferably from about 1% to about 30%, most preferably from about 5% to about 20% by weight, of a detersive surfactant, said detersive surfactant is selected from the group consisting of anionic, cationic, nonionic, zwitterionic, ampholytic surfactants, and mixtures thereof;

b) at least about 0.001 ppm, preferably from about 0.01 to about 10000 ppm, more preferably from about 0.1 to about 5000 ppm, most preferably form about 10 to about 1000 ppm, of a superoxide generator photochemical disinfectant having the formula:

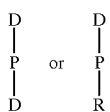

wherein P is a photosensitizing group; each D is independently a moiety which is capable of enhancing the production of singlet oxygen; and R is an axial moiety which mediates the solubility or substantivity of the super oxide generator as described herein above; and c) the balance carriers and adjunct materials, said adjunct ingredients are selected from the group consisting of buffers, builders, chelants, filler salts, soil release agents, dispersants, enzymes, enzyme boosters, perfumes, thickeners, abrasives, solvents, clays, and mixtures thereof.

The present invention also relates to a method for cleaning a stained fabric comprising contacting a stained fabric in need of cleaning with an aqueous cleaning solution comprising at least 0.001 ppm of a superoxide generator according to the present invention followed by exposing the surface of the treated fabric to a source of light having a minimal wavelength range from about 300 to about 1200 nanometers.

The present invention further relates to a method for cleaning a hard surface comprising contacting a hard surface in need of cleaning with an aqueous cleaning composition comprising at least 0.001 ppm of the superoxide generator according to the present invention and exposing the hard surface to a source of light having a minimal wavelength range from about 300 to about 1200 nanometers.

The present invention yet further relates to a method for cleaning a stained fabric with a cleaning material comprising a low aqueous cleaning composition comprising contacting a stained fabric in need of stain removal with a low aqueous cleaning solution comprising less than 50% water and at least 0.001 ppm of the superoxide generator according to the present invention followed by exposing the surface of the treated fabric to a source of light having a minimal wavelength range from about 300 to about 1200 nanometers.

The present invention still further relates to a method for cleaning a hard surface with a low aqueous cleaning composition comprising contacting a hard surface in need of cleaning with a low aqueous cleaning composition comprising less than 50% water and at least 0.001 ppm of the superoxide generator according to the present invention and exposing the hard surface to a source of light having a minimal wavelength range from about 300 to about 1200 nanometers.

Surfactant—The instant singlet oxygen generator containing compositions comprise from about 0.001% to about 60% by weight of a surfactant selected from the group consisting of anionic, nonionic, ampholytic and zwitterinonic surface active agents. For liquid systems, surfactant is preferably present to the extent of from about 0.1% to 20% by weight of the composition. For solid (i.e. granular) and viscous semi-solid (i.e. gelatinous, pastes, etc.) systems, surfactant is preferably-present to the extent of from about 1.5% to 30% by weight of the composition.

Nonlimiting examples of surfactants usefull herein typically at levels from about 1% to about 55%, by weight, include the conventional $C_{11}$–$C_{18}$ alkyl benzene sulfonates ("LAS") and primary, branched-chain and random $C_{10}$–$C_{20}$ alkyl sulfates ("AS"), the $C_{10}$–$C_{18}$ secondary (2,3) alkyl sulfates of the formula $CH_3(CH_2)_x(CHOSO_3^-M^+)$ $CH_3$ and $CH_3 (CH_2)_y(CHOSO_3^-M^+) CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1–7 ethoxy sulfates), $C_{10}$–$C_{18}$ alkyl alkoxy carboxylates (especially the EO 1–5 ethoxycarboxylates), the $C_{10}$–$C_{18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the socalled narrow peaked alkyl ethoxylates and $C_6$–$C_{12}$ alkyl phenol alkoxylates (especially ethoxylates and mixed ethoxy/propoxy), $C_{12}$–$C_{18}$ betaines and. sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides can also be used. Typical examples include the $C_{12}$–$C_{18}$ N-methylglucamides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the alkali metal salts, of organic sulfuric reaction products having in their molecular structure an alkyl radical containing from about 8 to about 22 carbon atoms and a radical selected from the group consisting of sulfonic acid and sulfuric acid ester radicals. (Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols ($C_{8–18}$ carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain from 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary allyl sulfates, such as those illustrated above, have the general formula ROSO3–M+ wherein R is typically a linear $C_{8-22}$ hydrocarbyl group and M is a water solubilizing cation. Branched chain primary alkyl sulfate surfactants (i.e., branched-chain "PAS") having 8–20 carbon atoms are also know; see, for example, Eur. Pat. Appl. 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

$$CH_3(CH_2)_n(CHOSO_3^-M^+)(CH_2)_mCH_3$$

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. The synthesis conducted in solvents which afford the secondary (2,3) alkyl sulfates on cooling, yields products which, when purified to remove the unreacted materials, randomly sulfated materials, unsulfated by-products such as C10 and higher alcohols, secondary olefin sulfonates, and the like, are typically 90+% pure mixtures of 2- and 3- sulfated materials (some sodium sulfate may be present) and are white, non tacky, apparently crystalline, solids. Some 2,3-disulfates may also be present, but generally comprise no more than 5% of the mixture of secondary (2,3) alkyl mono-sulfates. Such materials are available as under the name "DAN", e.g., "DAN 200" from Shell Oil Company.

ADJUNCT MATERIALS

Chelating Agents—The photo disinfectant compositions herein may also optionally contain one or more iron and/or manganese chelating agents. Such chelating agents can be selected from the group consisting of amino carboxylates, amino phosphonates, polyfunctionally-substituted aromatic chelating agents and mixtures therein, all as hereinafter defined. Without intending to be bound by theory, it is believed that certain chelating agents will interact with photodisinfectants of the present invention to increase their absorbency in the visible light spectrum. This is a process that is due to the ability of chelating agents to help effect the "substantiveness" of the compounds of the present invention.

Amino carboxylates useful as optional chelating agents include ethylene-diaminetetracetates, N-hydroxyethylethylenediaminetriacetates, nitrilotriacetates, ethylenediamine tetraproprionates, triethylenetet aminehexacetates, diethylenetrianinepentaacetates, and ethanoldiglycines, alkali metal, ammonium, and substituted amionium salts therein and mixtures therein.

A preferred biodegradable chelator for use herein is ethylenediamine disuccinate ("EDDS"), especially the [S,S] isomer as described in U.S. Pat. No. 4,704,233, Nov. 3, 1987, to Hartman and Perkins.

If utilized, these chelating agents will generally comprise from about 0.1% to about 10% by weight of the detergent compositions herein. More preferably, if utilized, the chelating agents will comprise from about 0.1% to about 3.0% by weight of such compositions Inert Salts. The inert salts (filler salts) used in the compositions of the present invention can be any water-soluble inorganic or organic salt or mixtures of such salts which do not destabilize any surfactant present. For the purposed of the present invention, "water-soluble" means having a solubility in water of at least 1 gram per 100 grams of water at 20° C. Examples of suitable salts include various alkali metal and/or alkali earth metal sulfate, chlorides, borates, bromides, fluorides, phosphates, carbonates, bicarbonates, citrates, acetates, lactates, etc.

Specific examples of suitable salts include sodium sulfate, sodium chloride, potassium chloride, sodium carbonate, potassium sulfate, lithium chloride, lithium sulfate, tripotassium phosphate, sodium borate, potassium bromide, potassium fluoride, sodium bicarbonate, magnesium sulfate, magnesium chloride, sodium citrate, sodium acetate, magnesium lactate, sodium fluoride. The preferred salts are inorganic salts preferably the alkali metal sulfates and chlorides. Particularly preferred salts, because of their low cost are sodium sulfate and sodium chloride. The salts are present in the compositions at levels of from 0% to 40%, preferably 10% to 20%.

EXAMPLE 1

Preparation of silicon phthalocyanine dichloride

To a mixture of 1,3-diiminoisoindoline (0.333 gm, 2.3 mmole) and anhydrous quinoline (15 mL) under argon blanketing is added silicon tetrachloride (1.1 g, 6.5 mmole). The mixture is lowered into an oil bath at 60° C. for 0.5 hr, heated to reflux over 0.5 hr, stirred at reflux for an additional 0.5 hr and cooled over 1 hr. To this solution is added methanol (10 mL) and the resultant mixture is allowed to stand at room temperature for 24 hr. The blue solid which forms upon standing is filtered off, rinsed twice with 10 mL portions of methanol, dried under vacuum at 120° C. and used without further purification.

The above procedure is suitable for use in preparing silicon naphthalocyanine dichloride using 1,3-diiminobenz-[f]-isoindoline.

EXAMPLE 2

Preparation of 1:3 silicon(VI)phthalo/ naphthalocyanine dichloride

To a mixture of 1,3-diiminoisoindoline (0.333 gm, 2.3 mmole), 1,3-diiminobenz[f]-isoindoline (1.35 gm, 6.9 mmole) and anhydrous quinoline (15 mL) under argon blanketing is added silicon tetrachloride (2.21 g, 12.9 mmole). The mixture is lowered into an oil bath at 60° C. for 0.5 hr, heated to reflux over 0.5 hr, stirred at reflux 0.5 hr and cooled over 1 hr. To this solution is added methanol (10 mL) and the resultant mixture is allowed stand at room temperature for 24 hr. The green solid which forms is removed by filtration, rsnsed twice with 10 mL portions of methanol, dried under vacuum at 120° C. and used without further purification.

EXAMPLE 3

Preparation of silicon phthalocyanine dihydroxide

Silicon (IV) phthalocyanine dichloride (2 gm, 3.3 mmole) is added to a refluxing solution of sodium methoxide (0.8 g, 14.8 mmole) in 95% wet ethanol (15 mL). The reaction mixture is refluxed 4 hr then cooled to room temperature. The resulting product is collected by filtration, rinsed with water and used without subsequent purification.

The above procedure is suitable for use in preparing silicon naphthalocyanine dihydroxide, and 1:3 silicon (IV) phthalo/naphthalocyanine dihydroxide.

EXAMPLE 4

Preparation of dilithium naphthalocyanine

To a refluxing solution of 2,3-dicyanonaphthalene (10 gm, 56.1 mmole) in anhydrous 1-butanol (300 mL) is added lithium shot (1.56 gm, 224.5 mmole). The solution is refluxed 6 hr under a blanket of argon after which time the solution is cooled, diluted with absolute methanol (500 mL) and allowed to stand at 0° C. for 18 hr. The green solid which results is collected by filtration, dried under vacuum at 80° C. and used without further purification.

The above procedure is suitable for use in preparing 1,4,8,11,15,18,22,25-octabutoxy-29,31-dilithium phthalocyanine from 3,6-dibutoxyphthalonitrile; 2,3,9,10,16,17,23,24-octachloro-29-31-dilithium phthalocyanine from 4,5-dichlorophthalonitrile; and tetrabutoxy-29,31-diithium phthalocyanine from 3-butoxyphthalonitrile wherein there is a mixture of isomers.

EXAMPLE 5

Preparation of naphthalocyanine

To a solution of dilithium naphthalocyanine (2 gm, 2.75 mmole) in N,N-Dimethylformnamide (200 mL) is added 1N hydrochloric acid (10 mL). The solution is stirred at room temperature for 1 hr. To this solution is added distilled water (200 mL) over approximately 0.5 hr. The green solid which forms is collected by filtration, dried under vacuum at 100° C. and used without further purification.

The above procedure is suitable for use in preparing 1,4,8,11,15,18,22,25-octabutoxy-29H,31H-phthalocyanine; 2,3,9,10,16,17,23,24-octachloro-29H,31H-phthalocyanine; and tetrabutoxy-29H,31H-phthalocyanine.

EXAMPLE 6

Preparation of silicon phthalocyanine-di-(triethanolamine)

A mixture of silicon phthalocyanine dihydroxide (0.25 gm, 0.44 mmole), anhydrous triethanolanine (10 gmn, 67 mmole) and xylenes (175 mL) is heated to reflux over 1.5 hr. The solution is continued at reflux for 2 hr. while water is removed by azeotropic distillation. The reaction mixture is then cooled and the solvent removed in vacuo. The resulting crude oil is dissolved in DMF (50 mL) and is added to water (800 mL) over about 0.5 hr. A blue solid which forms is collected by filtration, dried under vacuum at 80° C. and used without further purification.

The above procedure is suitable for use in preparing silicon naphthalocyanine-di-(triethanolamine) and 1:3 Silicon(VI)phthalo/naphthalocyanine-di-(triethanolamine). The cleaning compositions provided in accordance with this invention may be in the form of granules, liquids, bars, and the like, and typically are formulated to provide an in-use pH in the range of 9 to 11, however in the case of non-aqueous or low aqueous compositions the pH ranges may vary outside this range. Various carriers such as sodium sulfate, water, water-ethanol, BPP, MPP, EPP, PPP, sodium carbonate, and the like, may be used routinely to formulate the finished products. Granules may be produced by spray-drying or by agglomeration, using known techniques, to provide products in the density range of 350–950 g/l. Bars may be formulated using conventional extrusion techniques. The compositions may also contain conventional perfumes, bactericides, hydrotropes and the like. In the case of non-aqueous or low aqueous compositions, the cleaning compositions may be applied to an article which is used to deliver the compositions of the present invention to a fabric or to a hard surface. Non-limiting examples of compositions according to this invention are as follows:

| Ingredients | weight % | | | |
| --- | --- | --- | --- | --- |
| | 7 | 8 | 9 | 10 |
| Sodium LAS | 15 | 30 | 20 | 25 |
| NODAL | 1 | 1 | 1 | 1 |
| Alkyl Dimethyl Ammonium Chloride | 0.5 | 1 | 0.5 | 0.7 |
| Sodium Tripolyphosphate | 15 | 35 | 22 | 28 |
| Sodium Carbonate | 10 | 10 | 15 | 15 |
| SOKALAN | 2 | 2 | 2 | 2 |
| Carboxymethyl Cellulose | 1 | 1 | 1 | 1 |
| Tinopal CBS-X | 0.1 | 0.1 | 0.1 | 0.1 |
| Soil Release Agent[1] | 0.2 | 0.2 | 0.3 | 0.3 |
| Savinase 6.0T | 0.3 | 0.6 | 0.5 | 0.6 |
| BAN300T | 0.2 | 0.5 | 0.5 | 0.6 |
| Lipolase 100T | 0.1 | 0.2 | 0.2 | 0.3 |
| CAREZYME 5T | 0.1 | 0.2 | 0.2 | 0.3 |
| Sodium Perborate | — | — | 3.0 | 5.0 |
| NOBS | — | — | 2.0 | 3.0 |
| Photobleach[2] (ppm) | 0.005 | 0.01 | 0.008 | 0.01 |
| Moisture + SodiumSulfate + Perfume + Miscellaneous | Balance | Balance | Balance | Balance |

[1]Soil Release Agent according to U.S. Pat. No. 5,415,807 Gosselink et al., issued May 16, 1995.
[2]Photobleach according to Example 6.

What is claimed is:

1. A photochemical superoxide generator having the formula:

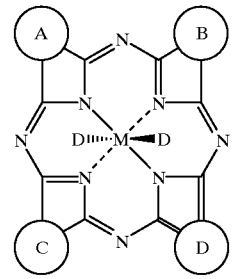

or the formula:

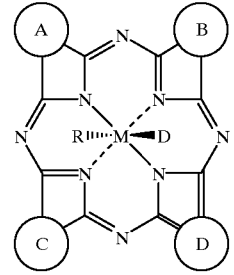

wherein M is a photoactive metal or non-metal having a valence greater than 3, rings A, B, C, and D are aromatic rings, each of said rings independently selected from the group consisting of:

i) a benzene ring unit having the formula:
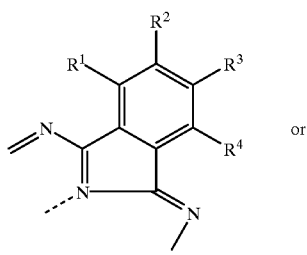
or
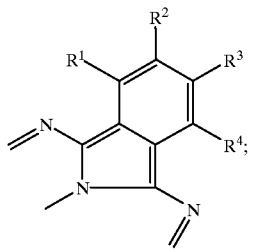
ii) a 2,3-naphthylene ring unit having the formula:
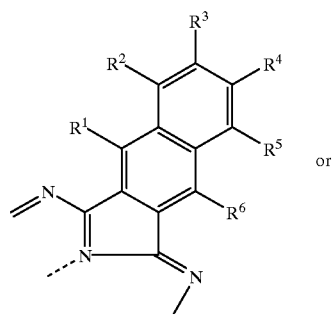
or
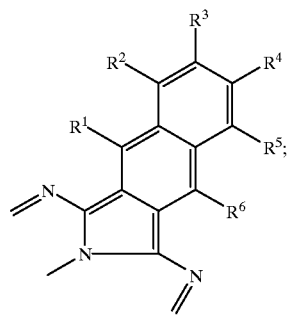
iii) a 1,2-naphthylene ring unit having the formula:
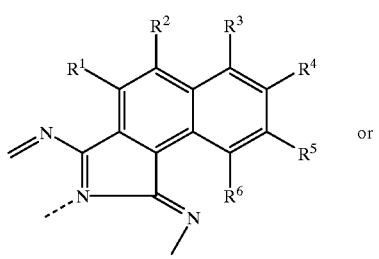
or
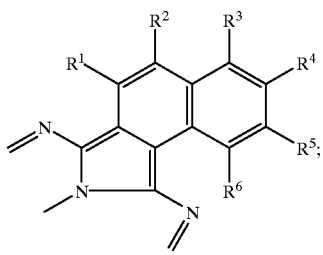
iv) an anthracene ring unit having the formula:
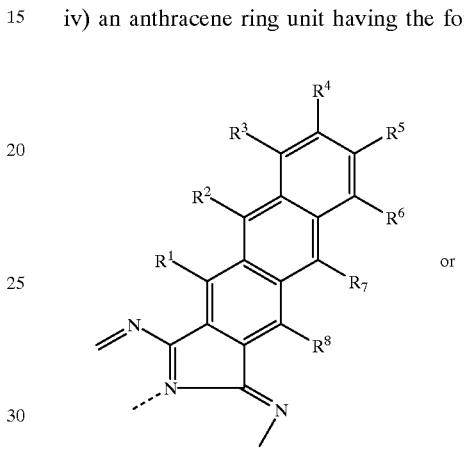
or
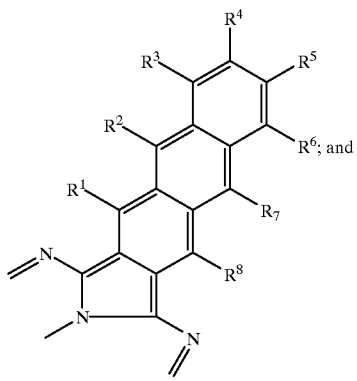; and
v) an phenanthrene ring unit having the formula:
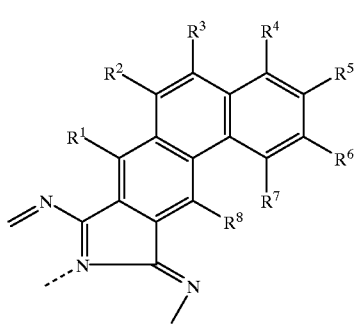
or -continued

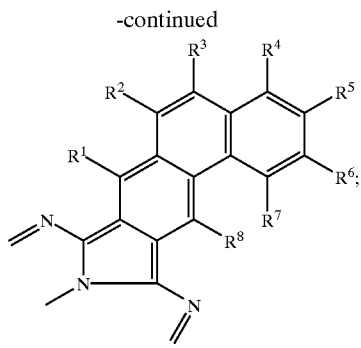

wherein each $R^1$, $R^2$, $R^3$, $R^4$, $R^5$, $R^6$, $R^7$, and $R^8$ unit is independently selected from the group consisting of:
a) hydrogen;
b) halogen;
c) hydroxy;
d) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
e) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
f) polyhydroxyl substituted $C_3$–$C_{22}$ alkyl;
g) $C_1$–$C_{22}$ alkoxy;
h) branched alkoxy having the formula:

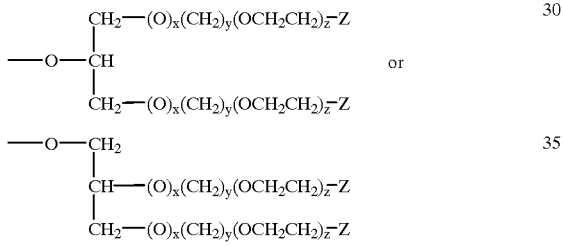

wherein Z is hydrogen, hydroxyl, $C_1$–$C_{30}$ alkyl, $C_1$–$C_{30}$ alkoxy, —$CO_2H$, —$OCH_2CO_2H$, —$SO_3^-M^+$, —$OSO_3^-M^+$, —$PO_3^{2-}M$, —$OPO_3^{2-}M$, or mixtures thereof; M is a water soluble cation in sufficient amount to satisfy charge balance; x is 0 or 1, each y independently has the value from 0 to 6, each z independently has the value from 0 to 100;
i) substituted aryl, unsubstituted aryl, or mixtures thereof;
j) substituted alkylenearyl, unsubstituted alkylenearyl, or mixtures thereof;
k) substituted aryloxy, unsubstituted aryloxy, or mixtures thereof;
l) substituted oxyalkylenearyl, unsubstituted oxyalkylenearyl, or mixtures thereof;
m) substituted alkyleneoxyaryl, unsubstituted alkyleneoxyaryl, or mixtures thereof;
n) $C_1$–$C_{22}$ thioalkyl, $C_3$–$C_{22}$ branched thioalkyl, or mixtures thereof;
o) an ester of the formula —$CO_2R^9$ wherein $R^9$ is
  i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  iii) polyhydroxyl substituted $C_3$–$C_{22}$ alkylene;
  iv) $C_3$–$C_{22}$ glycol;
  v) $C_1$–$C_{22}$ alkoxy;
  vi) $C_3$–$C_{22}$ branched alkoxy;
  vii) substituted aryl, unsubstituted aryl, or mixtures thereof;
  viii) substituted alkylenearyl, unsubstituted alkylenearyl, or mixtures thereof;
  ix) substituted aryloxy, unsubstituted aryloxy, or mixtures thereof;
  x) substituted oxyalkylenearyl, unsubstituted oxyalkylenearyl, or mixtures thereof;
  xi) substituted alkyleneoxyaryl, unsubstituted alkyleneoxyaryl, or mixtures thereof;
p) an alkyleneamino unit of the formula:

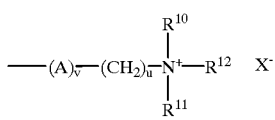

wherein $R^{10}$ and $R^{11}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
$R^{12}$ is:
  i) hydrogen;
  ii) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
  A is nitrogen or oxygen; X is chlorine, bromine, iodine, or other water soluble anion, v is 0 or 1, u is from 0 to 22;
q) an amino unit of the formula:

wherein $R^{17}$ and $R^{18}$ are $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
r) an alkylethyleneoxy unit of the formula:

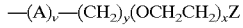

wherein Z is:
i) hydrogen;
ii) hydroxyl;
iii) —$CO_2H$;
iv) —$SO_3^-M^+$;
v) —$OSO_3^-M^+$;
vi) $C_1$–$C_6$ alkoxy;
vii) substituted aryl, unsubstituted aryl, or mixtures thereof;
viii) substituted aryloxy, unsubstituted aryloxy, or mixtures thereof;
ix) alkyleneamino; or mixtures thereof;
A is nitrogen or oxygen, M is a water soluble cation, v is 0 or 1, x is from 0 to 100, y is from 0 to 12;
s) substituted siloxy of the formula:

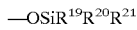

wherein each $R^{19}$, $R^{20}$, and $R^{21}$ is independently
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;

iv) an alkylethyleneoxy unit of the formula:

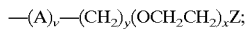

wherein Z is:
a) hydrogen;
b) hydroxyl;
c) —$CO_2H$;
d) —$SO_3^-M^+$;
e) —$OSO_3^-M^+$;
f) $C_1$–$C_6$ alkoxy;
g) substituted aryl, unsubstituted aryl, or mixtures thereof;
h) substituted aryloxy, unsubstituted aryloxy, or mixtures thereof;
i) alkyleneamino; or mixtures thereof;
A is nitrogen or oxygen, M is a water soluble cation, v is 0 or 1, x is from 0 to 100, y is from 0 to 12;
and mixtures thereof;
each D is independently a unit having the formula:

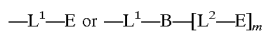

wherein B is a unit capable of providing a branch point wherein the branching unit has the formula:

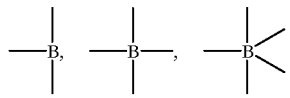

wherein B is an atom capable of forming from 3 to 5 covalent bonds to the $L^1$ and $L^2$ linking units, wherein B is selected from the group consisting of boron, aluminum, nitrogen, phosphorous, carbon, silicon, tin, germanium, and mixtures thereof; $L^1$ and $L^2$ are linking units and are independently selected from the group consisting of oxygen, $C_1$–$C_{18}$ linear or branched alkylene, $C_1$–$C_{18}$ linear or branched alkenylene; $C_1$–$C_{18}$ linear or branched alkyleneoxy, $C_1$–$C_{18}$ substituted or unsubstituted arylene, $C_1$–$C_{18}$ substituted or unsubstituted alkylenearylene, $C_1$–$C_{18}$ substituted or unsubstituted aryleneoxy, $C_1$–$C_{18}$ substituted or unsubstituted oxyalkylenearylene, $C_1$–$C_{18}$ substituted or unsubstituted alkyleneoxyarylene, and mixtures thereof; E units are electron transfer units having the formula:

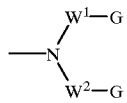

wherein each $W^1$ and $w^2$ is independently $C_1$–$C_4$ alkylene; G is hydrogen, an electron withdrawing group, and mixtures thereof; m is from 2 to 4; provided:
a) $L^1$, $L^2$, and B taken alone or in combination do not form a continuous series of conjugated bonds extending from the photosensitizing group P to the moiety E; and
b) the number of chemical bonds from photosensitizing group P to the E unit are no more than 20; and R is an axial moiety which mediates the solubility or substantivity of the superoxide generator and wherein each R unit is independently selected from the group consisting of:

a) hydrogen;
b) halogen;
c) hydroxyl;
d) cyano;
e) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
f) halogen substituted $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
g) polyhydroxyl substituted $C_3$–$C_{22}$ alkyl;
h) $C_1$–$C_{22}$ alkoxy;
i) branched alkoxy having the formula:

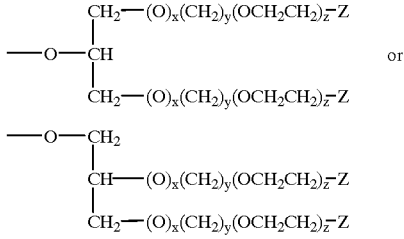

wherein Z is hydrogen, hydroxyl, $C_1$–$C_{30}$ alkyl, $C_1$–$C_{30}$ alkoxy, —$CO_2H$, —$CH_2CO_2H$, —$SO_3^-M^+$, —$OSO_3^-M^+$, —$PO_3^{2-}M$, —$OPO_3^{2-}M$, and mixtures thereof; M is a water soluble cation in sufficient amount to satisfy charge balance; x is 0 or 1, each y independently has the value from 0 to 6, each z independently has the value from 0 to 100;
j) substituted aryl, unsubstituted aryl, or mixtures thereof;
k) substituted alkylenearyl, unsubstituted alkylenearyl or mixtures thereof;
l) substituted aryloxy, unsubstituted aryloxy, of mixtures thereof;
m) substituted oxyalkylenearyl, unsubstituted oxyalkylenearyl, or mixtures thereof;
n) substituted alkyleneoxyaryl, unsubstituted alkyleneoxyaryl, or mixtures thereof;
o) $C_1$–$C_{22}$ thioalkyl, $C_4$–$C_{22}$ branched thioalkyl, or mixtures thereof;
p) an alkyleneamino unit of the formula:

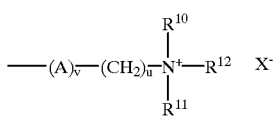

wherein $R^{10}$ and $R^{11}$ comprises $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
$R^{12}$ comprises:
i) hydrogen;
ii) $C_1$–$C_{22}$ alkyl, $C_4$–$C_{22}$ branched alkyl, $C_2$–$C_{22}$ alkenyl, $C_4$–$C_{22}$ branched alkenyl, or mixtures thereof;
A units comprise nitrogen or oxygen; X comprises chlorine, bromine, iodine, or other water soluble anion, v is 0 or 1, u is from 0 to 22;
q) an amino unit of the formula:

wherein $R^{17}$ and $R^{18}$ comprises $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;

r) an alkylethyleneoxy unit of the formula:

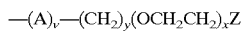

wherein Z comprises:
i) hydrogen;
ii) hydroxyl;
iii) —$CO_2H$;
iv) —$CH_2CO_2M$
v) —$SO_3$—$M^+$;
vi) —$OSO_3^-M^+$;
vii) $C_1$–$C_{30}$ alkoxy;
viii) substituted aryl, unsubstituted aryl, or mixtures thereof;
ix) substituted aryloxy, unsubstituted aryloxy, or mixtures thereof;
x) alkyleneamino; and mixtures thereof;
A comprises nitrogen or oxygen, M is a water soluble cation, v is 0 or 1, x is from 0 to 100, y is from 0 to 12;
s) carboxylate of the formula:

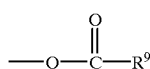

wherein $R^9$ comprises:
i) $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;
ii) halogen substituted $C_1$–$C_{22}$ alkyl, $C_3$–$C_{22}$ branched alkyl, $C_2$–$C_{22}$ alkenyl, $C_3$–$C_{22}$ branched alkenyl, and mixtures thereof;
iii) poly-hydroxyl substituted $C_3$–$C_{22}$ alkyl;
iv) $C_3$–$C_{22}$ glycol;
v) $C_1$–$C_{22}$ alkoxy;
vi) $C_4$–$C_{22}$ branched alkoxy;
vii) substituted aryl, unsubstituted aryl, or mixtures thereof;
viii) substituted alkylaryl, unsubstituted alkylaryl, or mixtures thereof;
ix) substituted aryloxy, unsubstituted aryloxy, or mixtures thereof;
x) substituted alkoxyaryl, unsubstituted alkoxyaryl, or mixtures thereof;
xi) substituted alkyleneoxyaryl, unsubstituted alkyleneoxyaryl, or mixtures thereof;
t) substituted siloxy of the formula:

—$OSiR^{19}R^{20}R^{21}$ wherein each $R^{19}$, $R^{20}$, and $R^{21}$ is independently selected from the group consisting of:
i) $C_1$–$C_{22}$ alkyl, $C_3$–$C_{22}$ branched alkyl, $C_2$–$C_{22}$ alkenyl, $C_3$–$C_{22}$ branched alkenyl, or mixtures thereof;
ii) substituted aryl, unsubstituted aryl, or mixtures thereof;
iii) substituted aryloxy, unsubstituted aryloxy, or mixtures thereof;
iv) an alkylethyleneoxy unit of the formula:

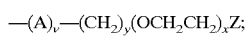

wherein Z comprises:
a) hydrogen;
b) $C_1$–$C_{30}$ alkyl;
c) hydroxyl;
d) —$CO_2M$;
e) —$CH_2CO_2M$;
f) —$SO_3^-M^+$;
g) —$OSO_3^-M^+$;
h) $C_1$–$C_6$ alkoxy;
i) substituted aryl, unsubstituted aryl, or mixtures thereof;
j) substituted aryloxy, unsubstituted aryloxy, or mixtures thereof;
k) alkyleneamino; or mixtures thereof;
A units comprise nitrogen or oxygen, M is a water soluble cation, v is 0 or 1, x is from 0 to 100, y is from 0 to 12; and mixtures thereof.

2. A compound according to claim 1 wherein G is selected from the group consisting of halogen, nitro, cyano, substituted or unsubstituted phenyl, hydroxyl, alkoxy, —$CO_2R^{29}$, —$CO_2M$, —$SO_3M$, —$OSO_3M$, —$PO_3M$, —$OPO_3M$, wherein $R^{29}$ is $C_1$–$C_{12}$ alkyl; alkyleneoxy units having the formula:

wherein $R^{28}$ is $C_1$–$C_4$ alkyl; Z is hydrogen, $C_1$–$C_{22}$ alkoxy, aryl, substituted aryl, aryloxy, substituted aryloxy, alkyleneamino, —$SO_3^-M^+$, —$OSO_3^-M^+$, —$CO_2H$, and mixtures thereof; the index x has the value from 1 to 4; i has the value from 0 to 20, the index j has the value from 0 to 20, the index k has the value from 0 to 20; alkyleneamino units having formula:

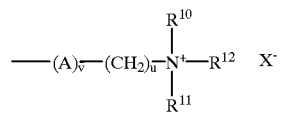

wherein $R^{10}$, and $R^{11}$ are each a $C_1$–$C_{22}$ alkyl, $C_3$–$C_{22}$ branched alkyl, $C_2$–$C_{22}$ alkenyl, $C_3$–$C_{22}$ branched alkenyl, $R^{12}$ is hydrogen, $C_1$–$C_{22}$ alkyl, $C_3$–$C_{22}$ branched alkyl, $C_2$–$C_{22}$ alkenyl, $C_3$–$C_{22}$ branched alkenyl and mixtures thereof A is the heteroatom nitrogen or oxygen, the index v is 0 when the heteroatom is absent, v is equal to 1 when the heteroatom is present, X is chloride, bromide, iodide, or other water soluble anion, u is from 0 to 22, and mixtures thereof.

3. A compound according to claim 2 wherein G is:
a) $C_1$–$C_{16}$ alkoxy;
b) hydroxy;
c) —$CO_2R^{29}$;
d) —$CO_2M$;
e) —$SO_3M$;
f) ethyleneoxy of the formula:

wherein Z is:
i) hydrogen;
ii) hydroxyl;
iii) $C_1$–$C_{22}$ alkoxy;
iv) —$CO_2M$;
v) —$CH_2CO_2M$;
vi) —$SO_3M$;

vii) —OSO$_3$M; or viii) alkyleneamino;

and mixtures thereof; M is hydrogen, a water soluble cation; x is from 1 to 20.

4. A compound according to claim 3 wherein the axial R units have the formula:

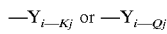
—Y$_{i-Kj}$ or —Y$_{i-Qj}$ wherein Y is a linking moiety selected from the group consisting of O, CR$^{25}$R$^{26}$, OSiR$^{25}$R$^{26}$, OSnR$^{25}$R$^{26}$, and mixtures thereof; wherein R$^{25}$ and R$^{26}$ are hydrogen, C$_1$–C$_4$ alkyl, halogen, and mixtures thereof; i is 0 or 1, j is from 1 to 3;

K is a ligand selected from the group consisting of:

a) C$_1$–C$_{30}$ linear alkyl, C$_3$–C$_{30}$ branched alkyl C$_2$–C$_{30}$ linear alkenyl, C$_3$–C$_{30}$ branched alkenyl, C$_6$–C$_{20}$ aryl, C$_7$–C$_{20}$ arylalkyl, C$_7$–C$_{20}$ alkylaryl;

b) an alkylethyleneoxy unit of the formula

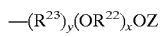
—(R$^{23}$)$_y$(OR$^{22}$)$_x$OZ wherein Z is hydrogen, C$_7$–C$_{20}$ alkyl C$_3$–C$_{20}$ branched alkyl, C$_2$–C$_{20}$ linear alkenyl, C$_3$–C$_{20}$ branched alkenyl, C$_6$–C$_{20}$ aryl, C$_7$–C$_{30}$ arylalkyl, C$_6$–C$_{20}$ alkylaryl; R$^{22}$ is C$_1$–C$_4$ linear alkylene, C$_1$–C$_4$ branched alkylene, C$_3$–C$_6$ hydroxyalkylene, and mixtures thereof; R$^{23}$ is selected from the group consisting of C$_2$–C$_{20}$ alkylene, C$_3$–C$_{20}$ branched alkylene, C$_6$–C$_{20}$ arylene, C$_7$–C$_{30}$ arylalkylene, C$_7$–C$_{30}$ alkylarylene; x is from 1 to 100; y is 0 or 1; and c) mixtures thereof;

Q is an ionic moiety having the formula:

—R$^{24}$—W wherein R$^{24}$ is selected from the group consisting of C$_3$–C$_{30}$ linear alkylene, C$_3$–C$_{30}$ branched alkylene, C$_2$–C$_{30}$ linear alkenylene, C$_3$–C$_{30}$ branched alkenylene, C$_6$–C$_{16}$ arylene, and mixtures thereof; W is selected from the group consisting of —CO$_2$$^-$M$^+$, —SO$_3$$^-$M$^+$, —OSO$_3$$^-$M$^+$; PO$_3$$^{2-}$M$^+$, —OPO$_3$$^-$M$^+$, alkyleneamino; M is a water soluble cation of sufficient charge to provide electronic neutrality and X is a water soluble anion.

5. A laundry detergent composition comprising:

a) at least about 0.1%, by weight, of a detersive surfactant, said detersive surfactant is selected from the group consisting of anionic, cationic, nonionic, zwitterionic, ampholytic surfactants, and mixtures thereof;

b) at least about 0.001 ppm of a photochemical superoxide generator as set forth in claim 1; and c) the balance carriers and adjunct ingredients.

6. A composition according to claim 5 wherein G is selected from the group consisting of halogen, nitro, cyano, substituted or unsubstituted phenyl, hydroxyl, alkoxy, —CO$_2$R$^{29}$, —CO$_2$M, —SO$_3$M, —OSO$_3$M, —PO$_3$M, —OPO$_3$M, wherein R$^{29}$ is C$_1$–C$_{12}$ alkyl; alkyleneoxy units having the formula:

——[O(CH$_2$)$_x$]$_i$——[O(CH$_2$CH)]$_j$ [O(CHCH$_2$)]$_k$Z
　　　　　　　　　　|　　　　　　|
　　　　　　　　　R$^{28}$　　　R$^{28}$ wherein R$^{28}$ is C$_1$–C$_4$ alkyl; Z is hydrogen, C$_1$–C$_{22}$ alkoxy, aryl, substituted aryl, aryloxy, substituted aryloxy, alkyleneamino, —SO$_3$$^-$M$^+$, —OSO$_3$$^-$M$^+$, —CO$_2$H, and mixtures thereof; the index x has the value from 1 to 4; i has the value from 0 to 20, the index j has the value from 0 to 20, the index k has the value from 0 to 20; alkyleneamino units having formula:

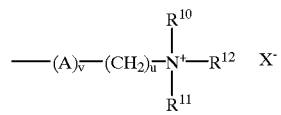
　　　　　　　　R$^{10}$
　　　　　　　　|
——(A)$_v$—(CH$_2$)$_u$—N$^+$—R$^{12}$　X$^-$
　　　　　　　　|
　　　　　　　　R$^{11}$ wherein R$^{10}$, and R$^{11}$ are each a C$_1$–C$_{22}$ alkyl, C$_3$–C$_{22}$ branched alkyl, C$_2$–C$_{22}$ alkenyl, C$_3$–C$_{22}$ branched alkenyl, R$^{12}$ is hydrogen, C$_1$–C$_{22}$ alkyl, C$_3$–C$_{22}$ branched alkyl, C$_2$–C$_{22}$ alkenyl, C$_3$–C$_{22}$ branched alkenyl and mixtures thereof, A is the heteroatom nitrogen or oxygen, the index v is 0 when the heteroatom is absent, v is equal to 1 when the heteroatom is present, X is chloride, bromide, iodide, or other water soluble anion, u is from 0 to 22, and mixtures thereof.

7. A composition according to claim 6 wherein G is:

a) C$_1$–C$_{16}$ alkoxy;

b) hydroxy;

c) —CO$_2$R$^{29}$;

d) —CO$_2$M;

e) —SO$_3$M;

f) ethyleneoxy of the formula:

—(OCH$_2$C$_2$)$_x$Z wherein Z is:

i) hydrogen;

ii) hydroxyl;

iii) C$_1$–C$_{22}$ alkoxy;

iv) —CO$_2$M;

v) —CH$_2$CO$_2$M;

vi) —SO$_3$M;

vii) —OSO$_3$M; or viii) alkyleneamino;

and mixtures thereof; M is hydrogen, a water soluble cation; x is from 1 to 20.

8. The composition of claim 5 wherein the photochemical superoxide generator is present in an amount of from about 0.001 ppm to about 10,000 ppm.

9. The composition of claim 5 wherein the detersive surfactant is present in an amount of from about 0.1% to about 30% by weight.

10. A composition according to claim 1 wherein the axial R units have the formula:

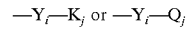
—Y$_i$—K$_j$ or —Y$_i$—Q$_j$ wherein Y is a linking moiety selected from the group consisting of O, CR$^{25}$R$^{26}$, OSiR$^{25}$R$^{26}$, OSnR$^{25}$R$^{26}$, and mixtures thereof; wherein R$^{25}$ and R$^{26}$ are hydrogen, C$_1$–C$_4$ alkyl, halogen, and mixtures thereof; i is 0 or 1, j is from 1 to 3;

K is a ligand selected from the group consisting of:

a) C$_1$–C$_{30}$ linear alkyl, C$_3$–C$_{30}$ branched alkyl, C$_2$–C$_{30}$ linear alkenyl, C$_3$–C$_{30}$ branched alkenyl, C$_6$–C$_{20}$ aryl, C$_7$–C$_{20}$ arylalkyl, C$_7$–C$_{20}$ alkylaryl;

b) an alkylethyleneoxy unit of the formula

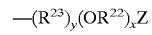
—(R$^{23}$)$_y$(OR$^{22}$)$_x$Z wherein Z is hydrogen, C$_7$–C$_{20}$ alkyl, C$_3$–C$_{20}$ branched alkyl, C$_2$–C$_{20}$ linear alkenyl, C$_3$–C$_{20}$ branched alkenyl, $C_6$–$C_{20}$ aryl, $C_7$–$C_{30}$ arylalkyl, $C_6$–$C_{20}$ alkylaryl; $R^{22}$ is $C_1$–$C_4$ linear alkylene, $C_1$–$C_4$ branched alkylene, $C_3$–$C_6$ hydroxyalkylene, and mixtures thereof; $R^{23}$ is selected from the group consisting of $C_2$–$C_{20}$ alkylene, $C_3$–$C_{20}$ branched alkylene, $C_6$–$C_{20}$ arylene, $C_7$–$C_{30}$ arylalkylene, $C_7$–$C_{30}$ alkylarylene; x is from 1 to 100; y is 0 or 1; and c) mixtures thereof;

Q is an ionic moiety having the formula:

wherein $R^{24}$ is selected from the group consisting of $C_3$–$C_{30}$ linear alkylene, $C_3$–$C_{30}$ branched alkylene, $C_2$–$C_{30}$ linear alkenylene, $C_3$–$C_{30}$ branched alkenylene, $C_6$–$C_{16}$ arylene, and mixtures thereof; W is selected from the group consisting of —$CO_2^-M^+$, —$SO_3^-M^+$, —$OSO_3^-M^+$; $PO_3^{2-}M^+$, —$OPO_3^-M^+$, alkyleneamino; M is a water soluble cation of sufficient charge to provide electronic neutrality and X is a water soluble anion.

11. A hard surface cleaning composition comprising:
a) at least about 0.1%, of a detersive surfactant, said detersive surfactant is selected from the group consisting of anionic, cationic, nonionic, zwitterionic, ampholytic surfactants, and mixtures thereof;
b) at least about 0.001 ppm, of a superoxide generator photochemical disinfectant according to claim 1; and
c) the balance carriers and adjunct materials, said adjunct ingredients are selected from the group consisting of buffers, builders, chelants, filler salts, soil release agents, dispersants, enzymes, enzyme boosters, perfumes, thickeners, abrasives, solvents, clays, and mixtures thereof.

12. The composition of claim 11 wherein the photochemical superoxide generator is present in an amount of from about 0.001 ppm to about 10,000 ppm.

13. The composition of claim 11 wherein the detersive surfactant is present in an amount of from about 0.1% to about 30% by weight.

14. A method for cleaning a stained fabric comprising contacting a stained fabric in need of cleaning with an aqueous cleaning solution comprising at least 0.001 ppm of the superoxide generator according to claim 1 followed by exposing the surface of the treated fabric to a source of light having a minimal wavelength range from about 300 to about 1200 nanometers.

15. A method for cleaning a hard surface comprising contacting a hard surface in need of cleaning with an aqueous cleaning composition comprising at least 0.001 ppm of the superoxide generator according to claim 1 and exposing the hard surface to a source of light having a minimal wavelength range from about 300 to about 1200 nanometers.

16. A method for cleaning a stained fabric with a cleaning material comprising a low aqueous cleaning composition comprising contacting a stained fabric in need of stain removal with a low aqueous cleaning solution comprising less than 50% water and at least 0.001 ppm of the superoxide generator according to claim 1 followed by exposing the surface of the treated fabric to a source of light having a minimal wavelength range from about 300 to about 1200 nanometers.

17. A method for cleaning a hard surface with a low aqueous cleaning composition comprising contacting a hard surface in need of cleaning with a low aqueous cleaning composition comprising less than 50% water and at least 0.001 ppm of the superoxide generator according to claim 1 and exposing the hard surface to a source of light having a minimal wavelength range from about 300 to about 1200 nanometers.

18. A method for generating superoxide molecules comprising exposing a photochemical superoxide generator according to claim 1 to a source of light having a minimal wavelength of from about 300 to about 1200 nanometers.

* * * * *